United States Patent
McNair et al.

(10) Patent No.: US 11,694,291 B1
(45) Date of Patent: *Jul. 4, 2023

(54) SECURITIZING AND TRADING HEALTH QUALITY CREDITS

(71) Applicant: CERNER INNOVATION, INC., Kansas City, KS (US)

(72) Inventors: Douglas S. McNair, Seattle, WA (US); Kiran Kambhampati, Overland Park, KS (US)

(73) Assignee: Oracle International Corporation, Redwood Shores, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/362,649

(22) Filed: Jun. 29, 2021

Related U.S. Application Data

(63) Continuation of application No. 16/454,316, filed on Jun. 27, 2019, now Pat. No. 11,069,013, which is a
(Continued)

(51) Int. Cl.
*G06Q 50/22* (2018.01)

(52) U.S. Cl.
CPC .................... *G06Q 50/22* (2013.01)

(58) Field of Classification Search
CPC ........ G06Q 50/22; G16H 10/00; G16H 10/20; G16H 10/40; G16H 10/60; G16H 10/65;
(Continued)

(56) References Cited

U.S. PATENT DOCUMENTS 10,198,499 B1 2/2019 Mcnair et al.
10,431,336 B1 10/2019 Murrish et al.
(Continued)

FOREIGN PATENT DOCUMENTS

WO WO-9927483 A1 * 6/1999 ............. G06Q 30/02

OTHER PUBLICATIONS

"ePlus Recognized by Everything Channel's CRN Magazine as One of the Top Healthcare VARs." By Staff. GlobeNewswire. Dec. 8, 2010. (Year: 2010).*

*Primary Examiner* — Linh Giang Le
(74) *Attorney, Agent, or Firm* — Kilpatrick Townsend & Stockton LLP

(57) ABSTRACT

A computer-implemented trading platform, system, and method are provided for facilitating the trading and accounting for health quality offsets. So-called "health quality credits" related to emissions of 'potentially avoidable complications' (PACs) or 'potentially avoidable mortality' (PAMs). Emissions trading or "cap-and-trade" is an administrative approach used to control emissions that degrade public-goods assets by providing economic incentives for achieving and sustaining economically significant reductions in the emissions of pollutants that impair public goods such as clean air or health. In one embodiment, a method of accounting for health quality offsets established in one or more offset markets includes registering a health quality offset to an owner thereof; assigning a unique identifier to the health quality offset; crediting a client account with the health quality offset; receiving notification of a trade between a buyer and a seller; if the seller has an amount of health quality offsets sufficient for the trade, adjusting buyer and seller accounts with corresponding credits and debits; otherwise, providing a notification of insufficient health quality offsets to carry out the trade.

19 Claims, 12 Drawing Sheets

Related U.S. Application Data continuation of application No. 13/573,711, filed on Oct. 3, 2012, now Pat. No. 10,339,618.

(60) Provisional application No. 61/542,586, filed on Oct. 3, 2011.

(58) Field of Classification Search
CPC ........ G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
IPC ..................................................... G06Q 50/22
See application file for complete search history.

(56) References Cited

U.S. PATENT DOCUMENTS

| | | | | |
|---|---|---|---|---|
| 2005/0228692 | A1* | 10/2005 | Hodgdon | G16H 10/40 |
| | | | | 705/2 |
| 2005/0234742 | A1 | 10/2005 | Hodgdon | |
| 2013/0096935 | A1* | 4/2013 | Saidel | G06Q 30/0207 |
| | | | | 705/2 |

* cited by examiner

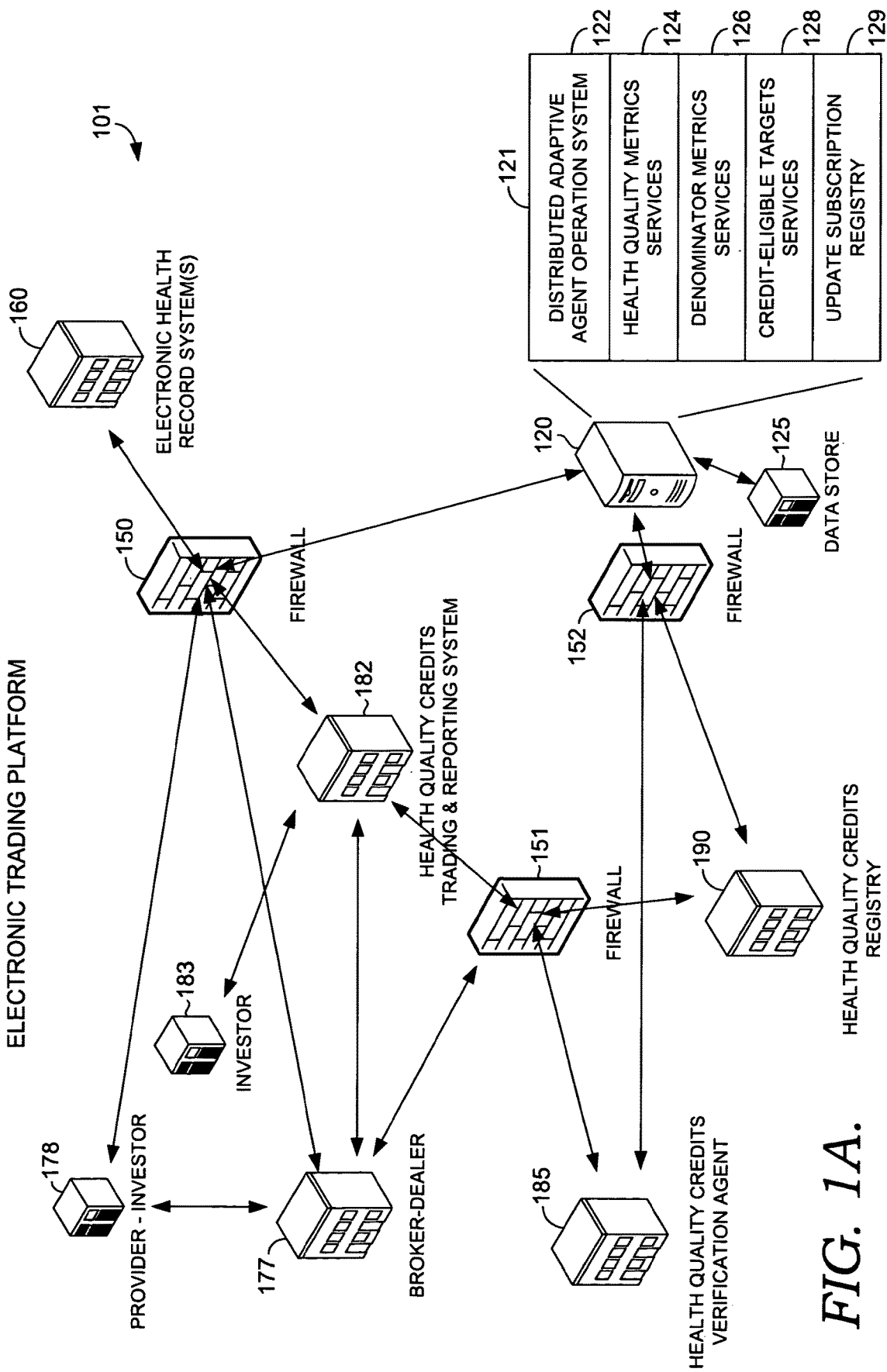

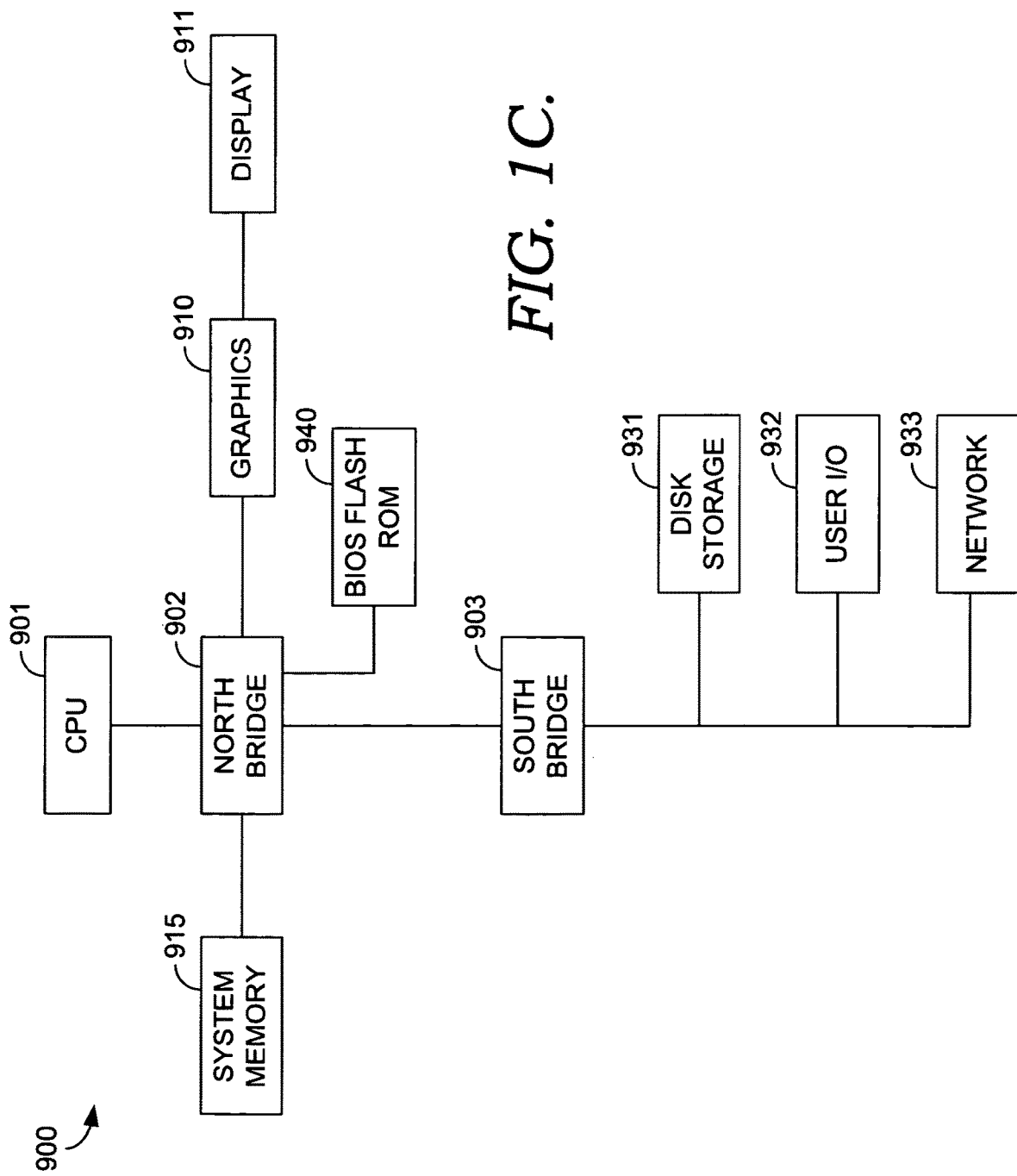

SECURITIZING AND TRADING HEALTH QUALITY CREDITS

CROSS-REFERENCE TO RELATED APPLICATIONS

This application is a continuation of, and claims priority from, U.S. patent application Ser. No. 16/454,316, filed on Jun. 27, 2019, entitled "Securitizing and Trading Health Quality Credits," which is a continuation of U.S. patent application Ser. No. 13/573,711, filed on Oct. 3, 2012, now U.S. Pat. No. 10,339,618, entitled "Securitizing and Trading Health Quality Credits," which claims the benefit of U.S. Provisional Application No. 61/542,586, titled "Securitizing And Trading Health Quality Credits," filed Oct. 3, 2011, all of which are hereby expressly incorporated by reference in their entireties.

INTRODUCTION

Health effects carry obvious economic implications. The price paid for inadequate emphasis on prevention includes the costs of excess medical care for avertable diseases and complications, as well as the deleterious economic effects of illness on a healthy workforce, corporate competitiveness, children's education, mental health, and community well-being.

Some estimates state that chronic illnesses cost the economy $4 in lost productivity for every $1 spent on health care. By making too little use of the forms of prevention that offer high economic value—greater health benefits per dollar—the opportunity to do more with the same resources, and to save more lives in the process, is also forfeited. This opportunity cost, albeit subtle, may be the more important economic price paid for inadequate emphasis on prevention. The majority of the $2 trillion that society spends annually on health care goes toward interventions of low-economic value (e.g., services costing $50,000 to $1 million per quality-adjusted life year, or QALY) gained. Services of high-economic value (e.g., costing less than $50,000 per QALY) represent the minority of health care services, of which only a small fraction are known to produce net savings (economic benefits that exceed the costs of delivery). Examples of the latter include childhood immunizations and counseling smokers to quit and interventions to mitigate obesity.

Taxation, financial incentives, and property rights legislation are options for internalizing externalities into the market. Excise taxes on tobacco to promote smoking cessation and fines if motorists fail to use seatbelts or put children passengers in approved car seats are examples of how externalities are dealt with in public health at a consumer level. Financial incentives to deal with other public health at a health services provider level remain relatively unexplored.

Under current market conditions and policies, health services providers have historically underinvested in high-quality care processes relative to the socially-preferred level for four reasons:

1. Private, for-profit firms are unlikely to capture the full financial return generated by their investment in health quality because there are externalities.
2. Public and private not-for-profit firms are unlikely to invest adequately in health quality, because of their inability to raise adequate capital in bond markets and unfavorable duration and convexity of debt instruments compared to the time-horizons of the improvements' returns.
3. Given the potential for free-riding, there is a possible second-mover advantage in the market for health improvement technologies. If plans and providers prefer to delay and imitate rather than innovate, the effect is that a majority will reduce or delay their investment, to the detriment of society overall.
4. The price of traditional care is artificially low and does not reflect the full cost to society from non-optimal health care system/process and foregone opportunities to prevent illness and promote health. This makes the price of acute-care and indemnity (traditional) care services abnormally low compared with what higher-quality care and preventive services would cost.

These four factors substantially impair the incentives for providers to innovate and to invest adequately in preventive and value-in-health technologies.

To mitigate these factors, Prometheus-type payment structures are one approach that internalizes certain externalities and offers more powerful financial incentives beyond conventional P4P. But new opportunities for private investment are needed, particularly securities that enable entities that outperform the field to experience larger long-term returns on their investment.

Accordingly, one way to accomplish this is to securitize high-quality health practices that are capable of optimizing health and preventing adverse outcomes, which although substantively different, may be understood as conceptually analogous to 'pollution' in environmental offsets exchanges. Creating securities that have equity-type properties to embody health quality is conceptually analogous to securitizing $CO_2$ emissions through trading of carbon offsets or CER credits. Under such schemes, health outcomes target limits transgressions and health quality target transgressions may be understood as being conceptually similar to transgression of $CO_2$ emissions caps.

SUMMARY

Systems, methods, and computer-readable media are provided for facilitating the securitization of health quality assets in a manner conceptually analogous to 'Cap and Trade' exchange mechanisms for trading environmental pollutant 'offsets' or 'credits'. In embodiments, the securities may be in the form of credits, which may be traded on a financial exchange and may be the subject of options and futures trading as well. So-called "health quality credits" related to emissions of 'potentially avoidable complications' (PACs) or 'potentially avoidable mortality' (PAMs). Some embodiments comprise a trading platform, and related system and method for trading and accounting for health quality offsets, such as voluntary health quality emission offsets trading. Some embodiments include a trading platform related system and method which accounts for different voluntary offset standards, and which consolidates a variety of pricing data. Some embodiments are directed to a computer-implemented trading platform and method that facilitates the trading of health quality offsets between buyers and sellers. In an embodiment, a system maintains safe custody of offset documentation and certificates, and reports trades to the appropriate national registry for regulated programs and, in a further aspect of an embodiment, the system may provide registry services for voluntary offset programs.

In one embodiment, a method of accounting for health quality offsets established in one or more offset markets includes registering a health quality offset to an owner thereof; assigning a unique identifier to the health quality offset; crediting a client account with the health quality offset; receiving notification of a trade between a buyer and a seller; adjusting buyer and seller accounts with corresponding credits and debits, if the seller has an amount of health quality offsets sufficient for the trade; otherwise, providing a notification of insufficient health quality offsets to carry out the trade.

In another embodiment, a method of trading and accounting for a health quality offset that may be established in one of any number of different offset markets includes registering, in a database, a plurality of health quality offsets each established in a particular one of two or more different offset markets; assigning each of said plurality of health quality offsets with a unique identifier; receiving a bid or ask quote for one of the plurality of health quality offsets; matching a buyer with a seller of said one of the plurality of health quality offsets based, at least in part, on the received bid or ask quote; if the seller has an amount of health quality offsets sufficient for the trade, executing a trade of said one of the plurality of health quality offsets between the buyer and the seller; and otherwise, providing a notification of insufficient health quality offsets to carry out the trade to at least the buyer and seller.

In another embodiment, a computer-implemented trading platform useful in trading and accounting for health quality offset trades made in two or more offset markets includes one or more processors; a memory operatively coupled to the one or more processors, said memory comprising a structured database therein configured to store information relating to two or more health quality offsets established in the two or more different offset markets; an interface to the one or more processors configured to receive a bid or ask quote for one of the two or more health quality offsets established in one of the two or more offset markets and to match a buyer with a seller of said one of the two or more health quality offsets based, at least in part, on the received bid or ask quote; wherein, if the seller has an amount of health quality offsets sufficient for the trade, the one or more processors execute a trade of said one of the two or more health quality offsets between the buyer and the seller, and otherwise, provide a notification of insufficient health quality offsets to carry out the trade to at least the buyer and seller.

In another embodiment, a method of converting a health quality offset credit includes retiring an offset credit verified under a first verification standard; verifying a new offset credit under a second verification standard, said new offset credit being essentially equivalent to the first offset credit at least in terms of representing a desired reduction in emissions; and thereafter, registering the new offset credit in a registry to a owner thereof. In another aspect of this embodiment, the first and second verification standards are different voluntary health quality offset standards.

BRIEF DESCRIPTION OF THE DRAWINGS

Embodiments of the invention are described in detail below with reference to the attached drawing figures, wherein:

FIGS. 1A, 1B, and 1C depict aspects of an illustrative operating environment suitable for practicing embodiments of a computer-implemented trading platform;

DETAILED DESCRIPTION

The subject matter of embodiments of our invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

Figure 1B:
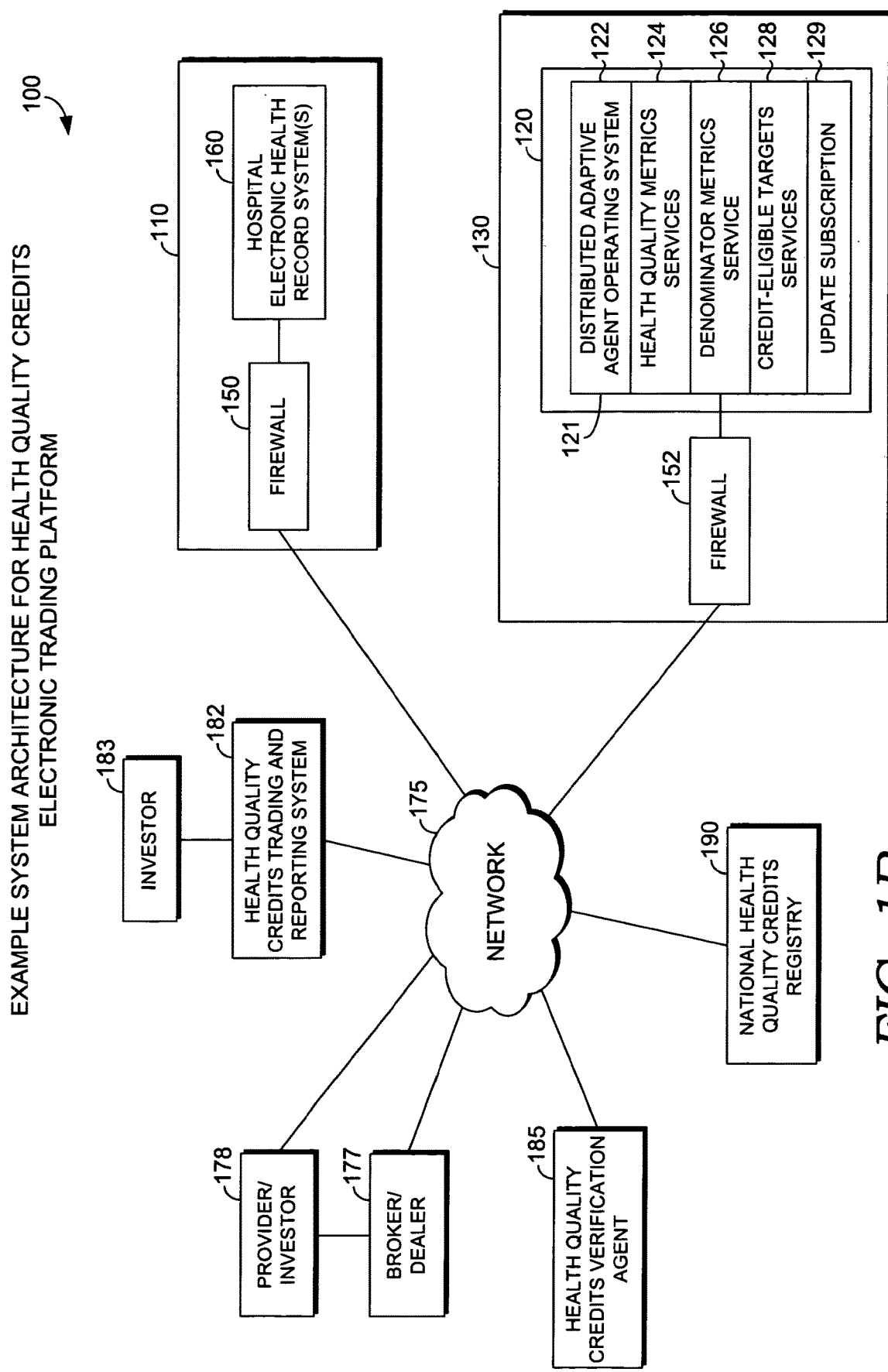

Turning now to FIGS. 1A and 1B, there is presented example operating environments suitable for practicing embodiments of the invention. With reference to FIG. 1A, the example operating environment includes a computerized system for carrying out an embodiment of a health quality credits electronic trading platform, herein referred to as platform 101. In this example operating environment, one or more electronic health record (EHR) systems 160 are communicatively coupled to a network behind firewall 150, which is communicatively coupled to computer system 120. In embodiments, EHR system 160 may comprise a Hospital EHR System, Ambulatory Clinic EHR System, Health Information Exchange, or other health records system that stores health care-related information including information about patient-treatment outcomes that may be used for identifying potentially avoidable patient mortalities and patient complications.

In embodiments, components of platform 101 are communicatively coupled over a local or distributed network (not shown) such as the Internet, a publicly-accessible network, or a private network. Embodiments of EHR system 160 include one or more data stores, such as data store 125, of health records and may further include one or more computers or servers that facilitate the storing and retrieval of the health records. Firewall 150 may comprise a separate firewall associated with each EHR system, in some embodiments. Furthermore, in some embodiments, one or more EHR systems may be located in the cloud or may be stored in data stores that are distributed across multiple physical locations. In some embodiments, EHR systems 160 further include record systems which store real-time or near real-time patient information, such as wearable, bedside, or in-home patient monitors, for example.

The operating environment of example platform 101 further includes computer system 120, which may take the form of a server, which is communicatively coupled through firewall 150 to EHR systems 160, and also through firewall 152 to health quality credits registry 190 and health quality credits verification agent 185. In embodiments, registry 190 may take the form of a database operating on a server or in the cloud. In some embodiments, registry 190 comprises a national registry, and in some embodiments registry 190 comprises multiple registries. Further, in some embodiments, each registry is associated with a particular class or type of health quality credit, such as mandatory or voluntary registries, or regional registries associated with regional health credits (credits associated with health care entities within a region). Registry 190 facilitates managing the trading of credits including tacking ownership, verifying, and retiring credits, preventing double-counting, and double-selling of credits.

Health quality credits verification agent 185 facilitates the verification of new health quality credits under one or more verification standards, verifying accreditation and/or supporting documentation related to projects undertaken for creating health quality offsets, credits, or reducing PAC and PAM emissions", and auditing support, in some embodiments. In some embodiments the standards used for verifying a health credit include existing standards such as JCAHO Core Measures, Centers for Medicare & Medicaid Services (CMS)'s 'Never Events' and 'Preventable Readmissions' criteria, and commercial payor's and plans' standards for chronic ambulatory care-sensitive conditions (for example, hemoglobin A1C targets for management of diabetics).

In some embodiments, verification agent 185 comprises one or more software applications, which may be embodied as one or more software agents, operating on a computer platform such as software stack 121. In some embodiments, verification agent 185 includes a user interface for facilitating the verification of offsets, accreditation, documentation, auditing, or other functions carried out by verification agent 185 discussed in connection to other drawings, by a user, while in some embodiments these operations are carried out by software routines or software agents.

Computer system 120 is further communicatively coupled through firewall 150 to provider-investor component 178, broker-dealer component 177, and health quality credits trading and reporting system (reporting system) 182. In embodiments, provider-investor 178 represents a health-care provider or insurance provider-investor component of the health quality credits electronic trading platform 101. Provider-investor 178 facilitates functions for investing or trading in health quality credits or offsets by a heath care entity, insurance company, or provider of other services associated with health care. For example, in one embodiment, provider-investor component 178 is associated with a hospital, and facilitates management of risk and liabilities (costs) including forecasting health-care market costs, and revenue generation by investing in health quality credits, which may be used or retired when needed by the hospital (for example, to reduce its PAM or PAC emissions) or traded on the market. In some embodiments, investor 178 takes the form of one or more software applications or software agents, with a user interface for facilitating monitoring and trading of health quality credits by a user.

Broker-dealer component 177 facilitates brokering health quality credits, trading, selling and buying credits, and other functions similar to a stock-exchange broker, and in some embodiments comprises one or more software applications or software agents operating on a server or computer system such as computer system 120, and having a user interface. Health quality credits trading and reporting system (reporting system) 182 facilitates reporting market data, trading, account statements, transactions history, position; as well as assigning an identifier to new credits; updating credit accounts to include newly issued credits; and reporting credit account updates, in some embodiments.

Reporting system 182 is communicatively coupled to investor component 183, broker-dealer component 177, verification agent 185 and registry 190, through firewall 151, and EHR systems 160, through firewall 150. In some embodiments, investor 183 takes the form of one or more software applications or software agents, with a user interface for facilitating monitoring and trading of health quality credits by a user. In some embodiments, the user interface is a Web-based graphical user interface that facilitates managing and trading of health credits for a user.

Embodiments of computer system 120 include computer software stack 121, which in some embodiments operates in the cloud, as a distributed system on a virtualization layer within computer system 120. Some embodiments of software stack 121 include a distributed adaptive agent operating system 122, which may be implemented as a platform in the cloud, and is capable of hosting a number of services such as 122, 124, 126, 128 and 129. Embodiments of services 122, 124, 126, 128 and 129 run as a local or distributed stack in the cloud, on one or more personal computers and servers such as computer system 120, and/or a computing component of provider-investor 178, investor 183, reporting system 182, registry 190, verification agent 185, broker-dealer component 177, or EHR systems 160. In one embodiment, these components, EHR systems 160, reporting system 182, registry 190 and/or software applications running on these components and systems, or user interfaces associated with these components and systems operate in conjunction with software stack 121.

In embodiments, health quality metrics services 124 facilitates discovery of the identity of (and quantitative and definitional information about) the variables that characterize quality- and safety-related health care occurrences or events that are the subject of quality measurement and credits issuance and exchange. Denominator metrics services 126 facilitates discovery of the identity of (and quantitative and definitional information about) the variables that characterize the population(s) in whom the quality metrics are measured. In some embodiments, the quality metrics are percentage or 'rate' measures, such as 'X number of events per Y denominator number of cases' in which those quality-related events arose. Credit-eligible services 128 provides a repository in which information for a plurality (or, potentially, 'all') current health quality-metrics for which credit-exchange programs exist are stored. In some embodiments, credit-eligible services 128 may also provide an archival storage for such information regarding programs or securities that are inactive or historical. Update subscription registry 129 provides entities engaged in publishing and/or subscribing to health quality metrics-related exchange to discover as well as to perform updates to existing records pertaining to those entities and their subordinate subscriptions or published metrics content.

In some embodiments, stack 121 includes additional services (not shown) for facilitating operations associated with health quality credit trading platform 101. For example, in some embodiments, a variables-indexing service and a Records/Documents ETL service provide services that facilitate retrieving frequent item sets, extracting database records, and cleaning the values of variables in records. In some embodiments these services are employed for automatically analyzing health record information to identify PAM or PAC emissions and information associated with projects undertaken for earning health quality offsets, or performance that qualifies for credit. In some embodiments, software services of stack 121 invoke other software services, and in some embodiments the software services are invoked by a software agent. Other services in some embodiments include statistical-computation and analyses packages such as, in one embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including LSA (latent semantic analysis), Weka (Weka datamining software services) or rWeka or similar collection of machine-learning algorithms for data mining, synonymy matching, and ontology mapping, including algorithms for data preprocessing, classification, regression, clustering, and association rules, arules, and Snowball package (Snowball stemmers developed by Kurt Hornik as part of the R-Project). Additional software services associated with some embodiments of stack 121 include Apache Hadoop and Hbase framework, or similar frameworks operable for providing a distributed file system.

Example operating environment 101 also includes data store 125, which in some embodiments includes health records including information associated with PAMs and PACs, health quality credits data, credit ownership data, credit accounts transaction histories, data associated with project accreditation and documentation, patient data and information; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers, and other similar information for software applications, routines, and agents; patient-derived data; insurance-provider information, and health care provider information, for example. In some embodiments, data store 125 comprises the data stores associated with the one or more of the systems and components of platform 101. For example in one embodiment, data store 125 includes the data store associated with an EHR system 160. Further, although depicted as a single data store, data store 125 may comprise one or more data stores, or may be in the cloud. Additional functions performed or facilitated by components of 101 described in connection to FIGS. 2-10.

FIG. 1B illustratively depicts another aspect of an example operating environment suitable for operating an embodiment of a health quality credits electronic trading platform, and referred to herein as 100. Within platform 100, a first premise location 110 includes a network behind firewall 150 communicatively coupled to network 175. In some embodiments, network 175 includes the Internet, a public network, or a private network. Premise location 110, which may comprise multiple separate geographical locations, further includes EHR system 160, which may comprise multiple separate EHR systems communicatively coupled through a network. In some embodiments, premise location 110 also includes a client interface (not shown), which communicates with EHR system 160. In some embodiments, interface takes the form of a user interface operated by a software application or set of applications on a client computing device such as a personal computer, laptop, smart phone, or tablet computing device. In one embodiment, the application includes the PowerChart solution suite, manufactured by Cerner Corporation. In one embodiment, the application is a Web-based application or applet. In some embodiments some or all of the components and systems of platform 100 include similar user interfaces.

Example environment 100 further includes a premise location 130 which includes computer system 120 communicatively coupled through firewall 152 to network 175. Additional numbered components of platform 100 in FIG. 1B are described in connection to FIG. 1A. In some embodiments, a server such as computer system 120, communicates through firewall 152, and remote firewall such as 150 to obtain records from an EHR system 160. In some embodiments, one or more software agents, applications, or software routines associated with stack 121 access information in a data store (not shown) such as data store 125, which is accessible to computer-system 120 and other components and systems of platform 100.

Turning now to FIG. 1C, there is shown one example of an embodiment of computer system 900 that has software instructions for storage of data and programs in computer-readable media. Computer system 900 is representative of a system architecture that is suitable for computer systems such as computer system 120 of FIGS. 1A and 1B, and the computer device(s) associated with other components of example platforms 100 and 101, in some embodiments. One or more CPUs such as 901, have internal memory for storage and couple to the north bridge device 902, allowing CPU 901 to store instructions and data elements in system memory 915, or, in some embodiments, memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1C is provided as one example of any number of computer architectures, such as computing architectures that support local, distributed, or cloud-based software platforms, and are suitable for supporting computer system 120 of FIGS. 1A and 1B.

In some embodiments, computing system 900 is a computing system made up of one or more computing devices. In an embodiment, computing system 900 includes an adaptive multi-agent operating system, but it will be appreciated that computing system 900 may also take the form of an adaptive single agent system or a non-agent system. Computing system 900 may be a distributed computing system, a data processing system, a centralized computing system, a single computer such as a desktop or laptop computer or a networked computing system.

In some embodiments, computing system 900 is a multi-agent computer system with software agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control, which promotes the concept of autonomy. Additional information about the capabilities and functionality of agents and distributed multi-agent operating systems, as they relate to these embodiments, is provided in U.S. patent application Ser. No. 13/250,072, filed on Sep. 30, 2011, which is herein incorporated by reference in its entirety.

FIGS. 2-10 provide a series of flow diagrams illustratively depicting embodiments of methods for facilitating health care including in ambulatory contexts and acute-care hospital settings, by securitizing assets and liabilities that arise for health provider enterprises in the course of delivering care services and preventive services. As shown in these drawings, where a component or system from FIGS. 1A and 1B, facilitates a particular step, operation, or functional relationship, this association is graphically shown by either including the step in dashed box identified with the component (for example, see FIG. 4 at step 420, which is associated with the verification agent) or by positioning the step at a horizontal level corresponding to an identification of the component, located on the left-hand side of the FIG. For example, in FIG. 10, step 1010 of "aggregating transactions for reporting period" is facilitated by a reporting system 182, shown along the left-hand side of FIG. 10, and the same horizontal level as step 1010.

Figure 2:
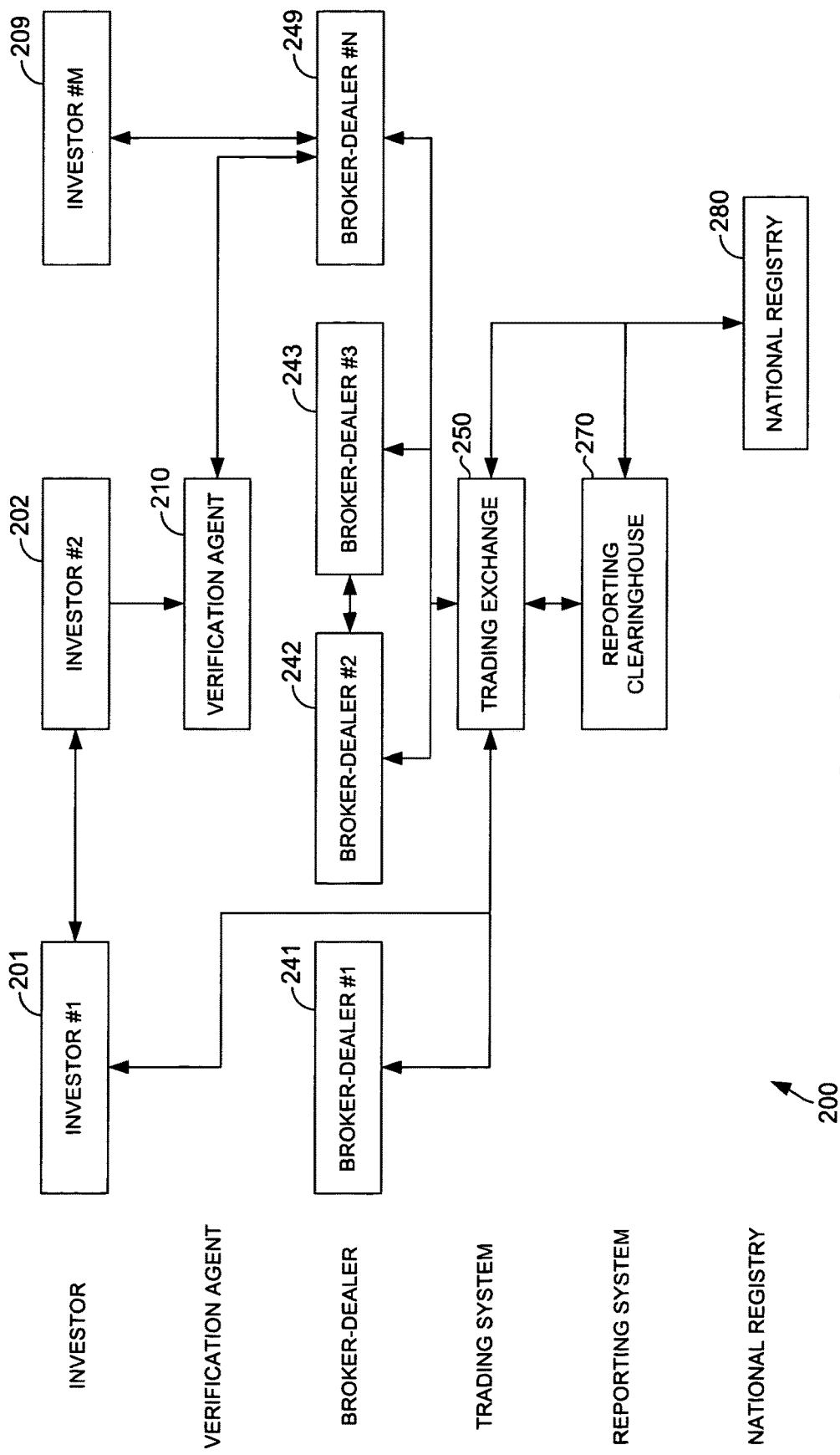
FIG. 2 depicts a process flow including functional relationships of an example embodiment of a trading platform directed to primary registration functions and secondary trading functions.

Turning now to FIG. 2, a process flow of an embodiment of a trading platform directed to primary registration functions and secondary trading functions is provided and referred to as 200. Process flow 200 depicts the functional relationships of entities, components, and systems that facilitate primary registration and trading, and further shows aspects of interaction among the methods provided in FIGS. 3 through 10. With reference to FIG. 2, a number of investor components (investors), such as 201, 202, and 209, facilitate buying and selling health quality credits, and may be embodied as investor components 178 or 183 of FIGS. 1A and 1B. For example, in some embodiments, an investor 201, 202, or 209 receives a request from a user, through a user interface, to buy or sell health quality credits, a request for market information such as prices and options, or in the case of a provider-investor, offset-generating project documentation for accreditation, and facilitates communicating that request to a broker-dealer component 241, 242, 243, or 249 or documentation to verification agent 210. In some scenarios, investor 201 and investor 202 may facilitate a trade of either of credits, cash, or other health quality securities between two parties or accounts, one associated with 201 and the other with 202, as indicated by the two-headed arrow between 201 and 202. In embodiments handling such a scenario, at least one of the parties will need to ascertain the validity of the credit that is the subject of the transaction, which is facilitated by verification agent at 210. In some embodiments, these participating investor components may or may not be associated with health provider organizations, but might optionally be associated with other qualified, interested parties who wish to speculate in health-related transactions.

Verification agent 210, which may be embodied as verification agent 185 of FIG. 1A or 1B, receives and verifies documentation submitted by an investor, such as investor 202. In some embodiments, verification agent 210 examines documentation and information that attest to the member/subscriber-in-good-standing status of a credit-holder, and to the authenticity of the credits and the unused balance of the credits that are asserted in the proposed exchange transaction. Broker-Dealer components (broker-dealers) 241, 242, 243, or 249, which may be embodied as 177 of FIGS. 1A and 1B, receive requests from investors 201, 202, or 209, and facilitate satisfying the requests through posting bid-ask quotes for credits through trading exchange 250. In some scenarios, a broker-dealer component, such as at 242 or 243, may facilitate engaging with another broker dealer component (as indicated by the example by-directional arrow between broker-dealer at 242 and broker-dealer at 243) for portfolio-balancing, market-making, or other purposes, as well as to transact trades of health quality credits. Trade exchange 250 facilitates matching buyers with sellers; executing trades including generating trade instructions; verifying buyer and seller accounts and recording settlement amounts, in some embodiments.

Figure 9:
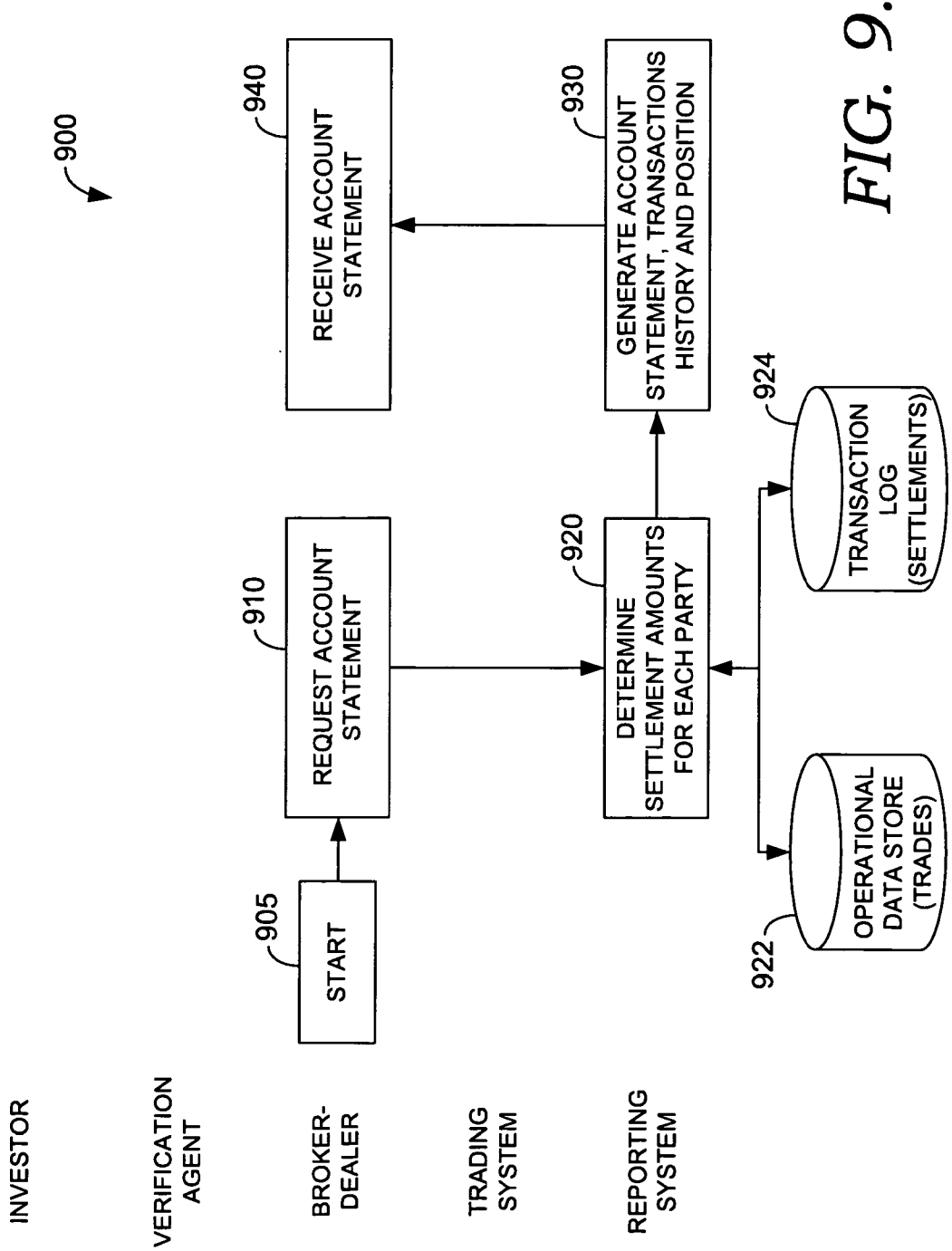
FIG. 9 depicts a flow diagram of a method for reporting, in accordance with an embodiment of the invention.
Figure 10:
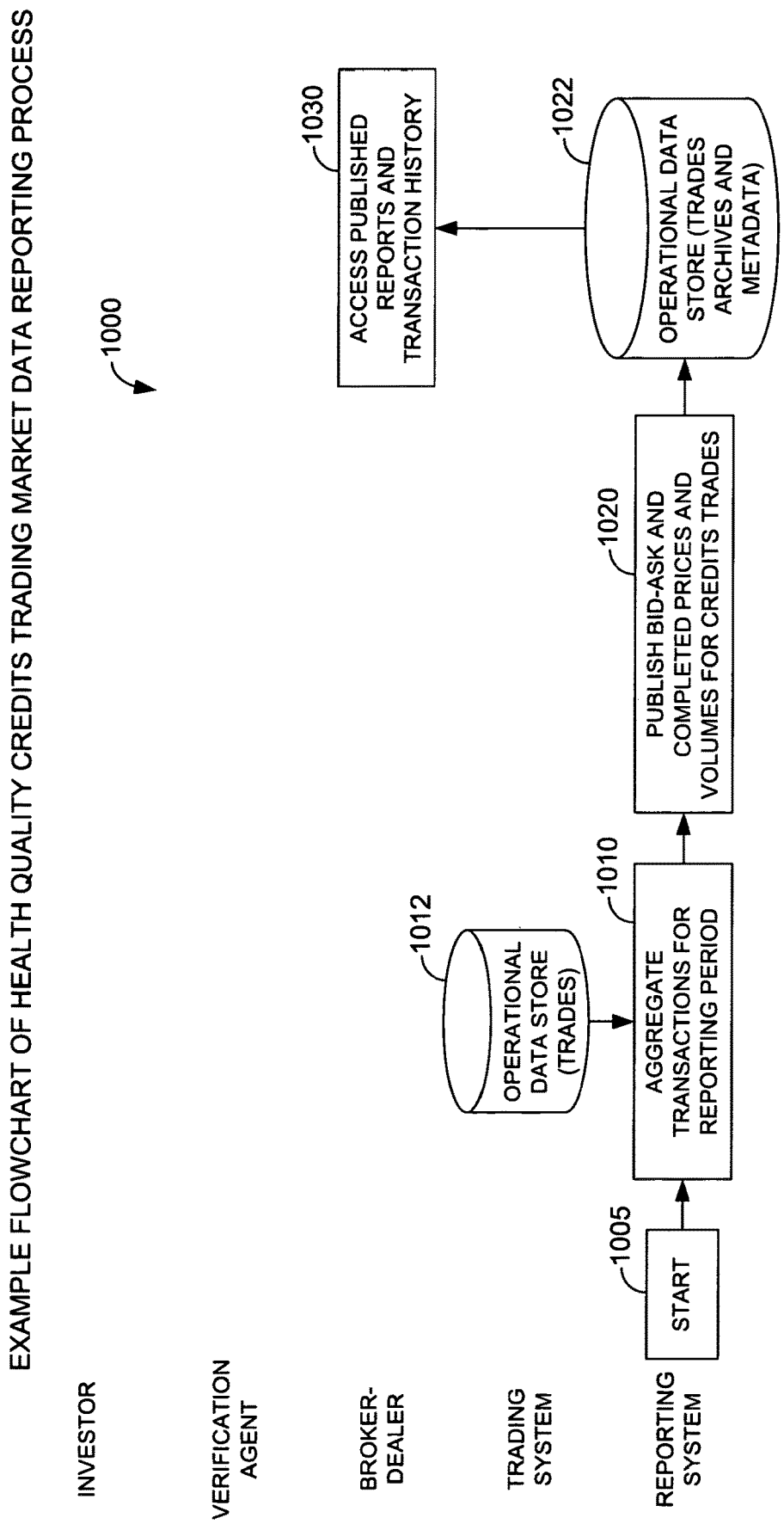
FIG. 10 depicts a flow diagram illustrating a method for market-data reporting, in accordance with an embodiment of the invention.

Process flow 200 includes a process at 250 where trade information is reported at a reporting clearing house. In some embodiments, reporting clearing house 270 comprises reporting system 182, and facilitates reporting market data, trading, account statements, transactions history, position, as well as assigning an identifier to new credits, updating credit accounts to include newly issued credits, and reporting credit account updates. FIGS. 9 and 10 provide additional examples of functions carried out by a reporting system such as system 182 or functions carried out at reporting clearing house 270.

Process flow 200 further includes registration functions carried out by national registry at 280, which in embodiments may be embodied as registry 190 of FIG. 1A or 1B.

In some embodiments including those having mandatory markets, each entity that participates in a mandatory health quality emission reduction framework and health quality emissions trading scheme maintains its emission allowances or "health quality credits" on the behalf of companies and the government in an electronic account known as a national registry. Additionally, as described in connection to FIGS. 3 and 4, various entities are also joined by the registry of the Quality Development Mechanism (QDM), which holds health quality credits generated by QDM projects on behalf of project sponsors. In embodiments where there are voluntary markets, voluntary registries may also be used. In some embodiments of both mandatory or voluntary markets, as a credit is "retired," the registries are updated accordingly. In some embodiments, computer interfaces may be used by various registries to supplement and/or replace a paper and facsimile system.

Embodiments of process flow 200 are directed to a computer-implemented trading platform, system, and method useful in the trading and accounting for health quality offsets, for example, so-called "health quality credits" related to emissions of 'potentially avoidable complications' (PACs) or 'potentially avoidable mortality' (PAMs). In some embodiments, an authority, which may be associated with a national registry, sets forth criteria for whether certain types PAMs, PACs, or other potentially avoidable patient outcomes are counted as an emission. In some embodiments, the verification agent, software agents, or other components running software routines, have certain capabilities to ascertain the veracity and accuracy of PAC and PAM and credit attribution. Thus for example, as further described below, in some embodiments an emission (or emission count) may be identifiable by determining the presence of a PAM, PAC, or other potentially avoidable patient outcome in a health care entity's health records. But in cases of dispute, an authority associated with a national registry may provide as an ultimate arbiter (in conjunction with the relevant Court). Emissions trading or "cap-and-trade" is an administrative approach used to control emissions that degrade public-goods assets by providing economic incentives for achieving and sustaining economically significant reductions in the emissions of pollutants that impair public goods such as clean air or health.

To engage in commercial enterprise is, inevitably, to produce some 'pollution.' Likewise, to engage in providing care services is, inevitably, to incur some adverse events or quality deficiencies. That is, not all PACs and PAMs events that are theoretically preventable will be prevented in each and every instance. Materialized PAC and PAM events scale with the volume of the health enterprise as well as with the population's burden of illness and severity of illness.

To be 'emissions-neutral', in a public health sense, is to not create more health quality 'emissions' ('pollution') than you remove or prevent. Quality-deficiency neutrality means, by definition, that incremental adverse outcomes from health services activity are equal to, and are offset by, adverse outcomes prevented by such activity. Accounting for health quality offsets can be conducted in a time-dependent manner similar to carbon offsets accounting. Thus, expenditures in the present accounting period that prevent future adverse events (e.g., by preventive services and healthy lifestyle and screening/monitoring) can earn health quality credits in the current period or in the (trailing) subsequent period, in addition to credits arising from adverse events interdicted by those expenditures during the current period.

In some embodiments, a market failure could occur with missing markets, e.g., a market in health quality property rights. Health quality trading creates incentives to reduce "pollution"; in some embodiments, 'caps' are set on the "emissions." Accordingly, this creates the scarcity required for a market.

Prior initiatives attempting to apply health quality offsetting and pay-for-performance (P4P) incentives, which compensate physicians or hospitals, have failed to cause widespread implementation of transformative, quality-revolutionizing changes. Even scenarios having relatively generous P4P incentives appear unable to materially improve quality and health outcomes.

Paradoxically, certain unintended consequences of some hospital quality measures have adversely affected patient care. For example, the requirement to give the first antibiotic dose in the emergency department within 4 hours if the patient has pneumonia has caused a precipitous increase in the rate of pneumonia misdiagnosis as providers sought to escape being penalized. Such effects severely constrain the rate of implementation of beneficial changes in health systems and processes.

To be meaningful, any sustainable emission reduction effort should instead be implemented by a market driven approach, as presented in embodiments herein, that provides economic incentives for compliance. This is particularly true for the generally unregulated voluntary offset market in which market transparency is necessary for investors/traders to have faith in offset pricing mechanisms and the underlying quality of the offset. Capturing offset data and accounting for the variety of mandatory and voluntary emission offsets and their various standards for investors and traders can be difficult, but it is practical to do with contemporary health information systems. It is necessary to capture and audit such data efficiently and timely to ensure liquidity and transparency in health quality offset trading. Some embodiments of our invention facilitate this by employing software agents of a multi-agent computer system 120 that are capable of efficiently and timely recognizing, capturing, and auditing such data.

Figure 4:
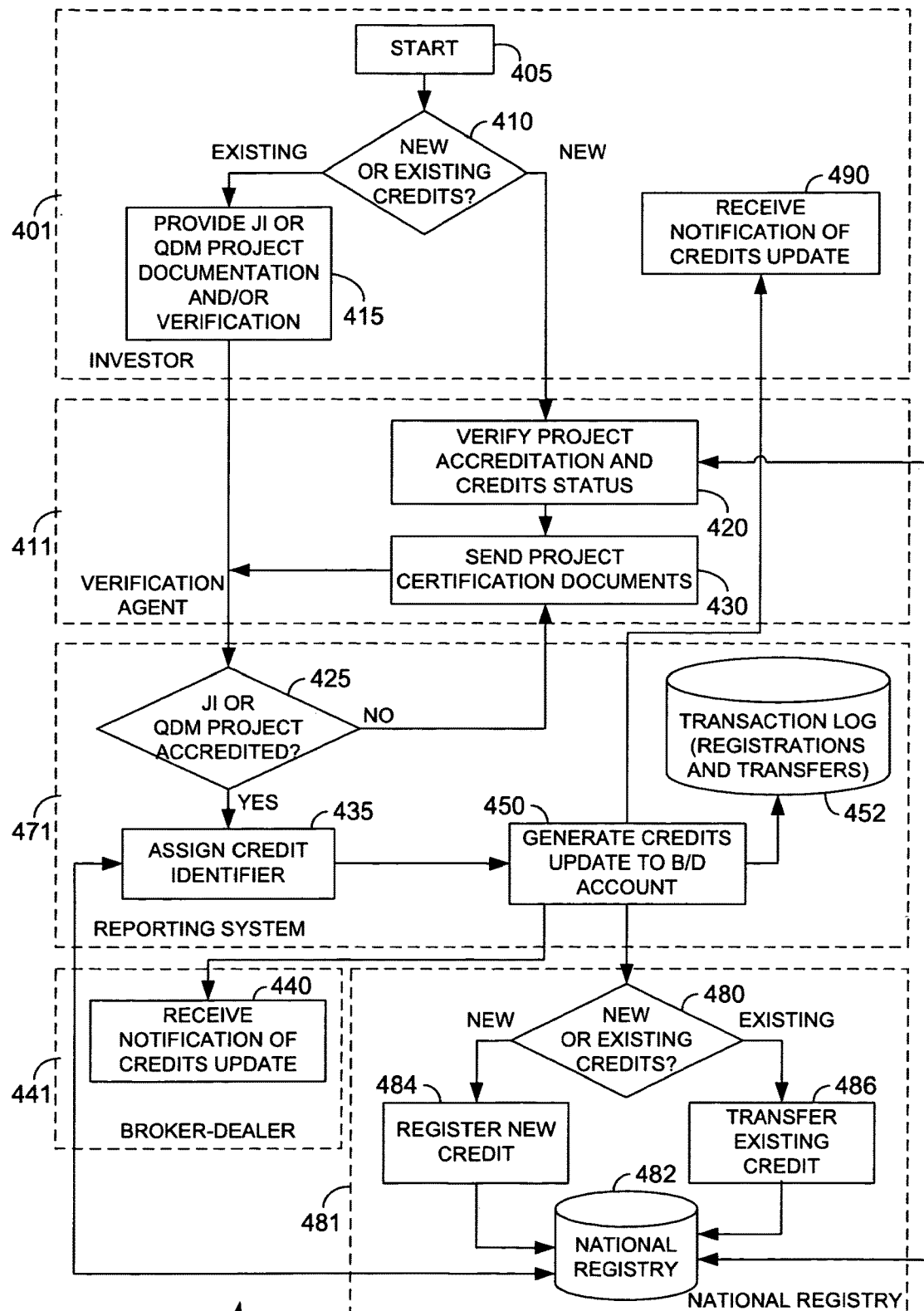
FIG. 4 depicts a flow diagram of a method for registering mandated or regulated offsets, in accordance with an embodiment of the invention.
Figure 5:
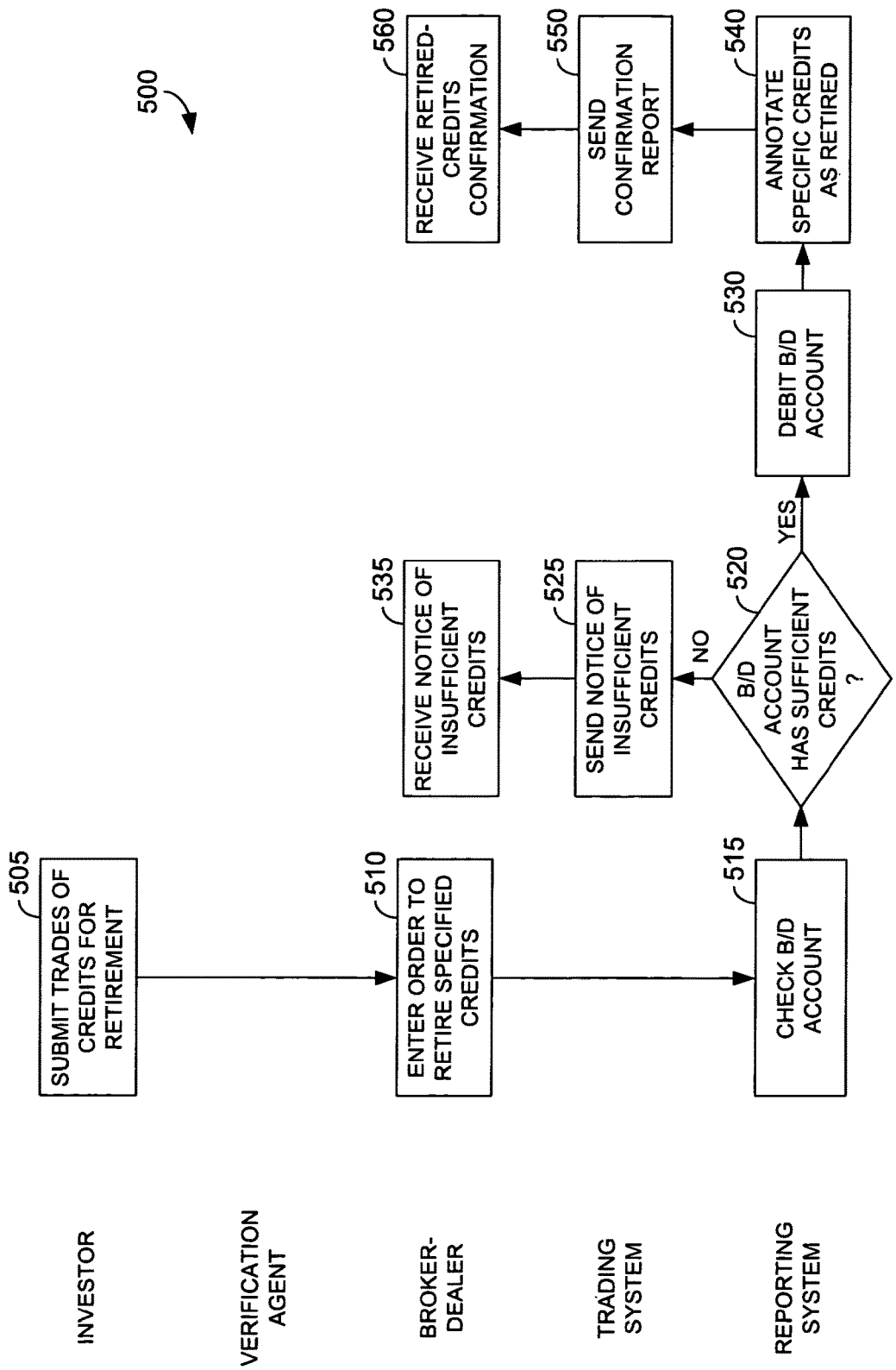
FIG. 5 depicts a flow diagram of a method for retiring health quality credits, in accordance with an embodiment of the invention.

Transparency applies not only to the valuation of mandatory and voluntary offsets, but to the related aspects of the underlying standards to which an offset was initially verified (as described in FIGS. 3 and 4) to ensure that an offset is "real" and offers true net "additionality," for example, and also ensures that no double counting is allowed when an offset is created or "retired" (as described in FIG. 5). Providing such transparency works to ensure a liquid market where buyers and sellers can freely engage with acceptable investment risk.

Figure 6:
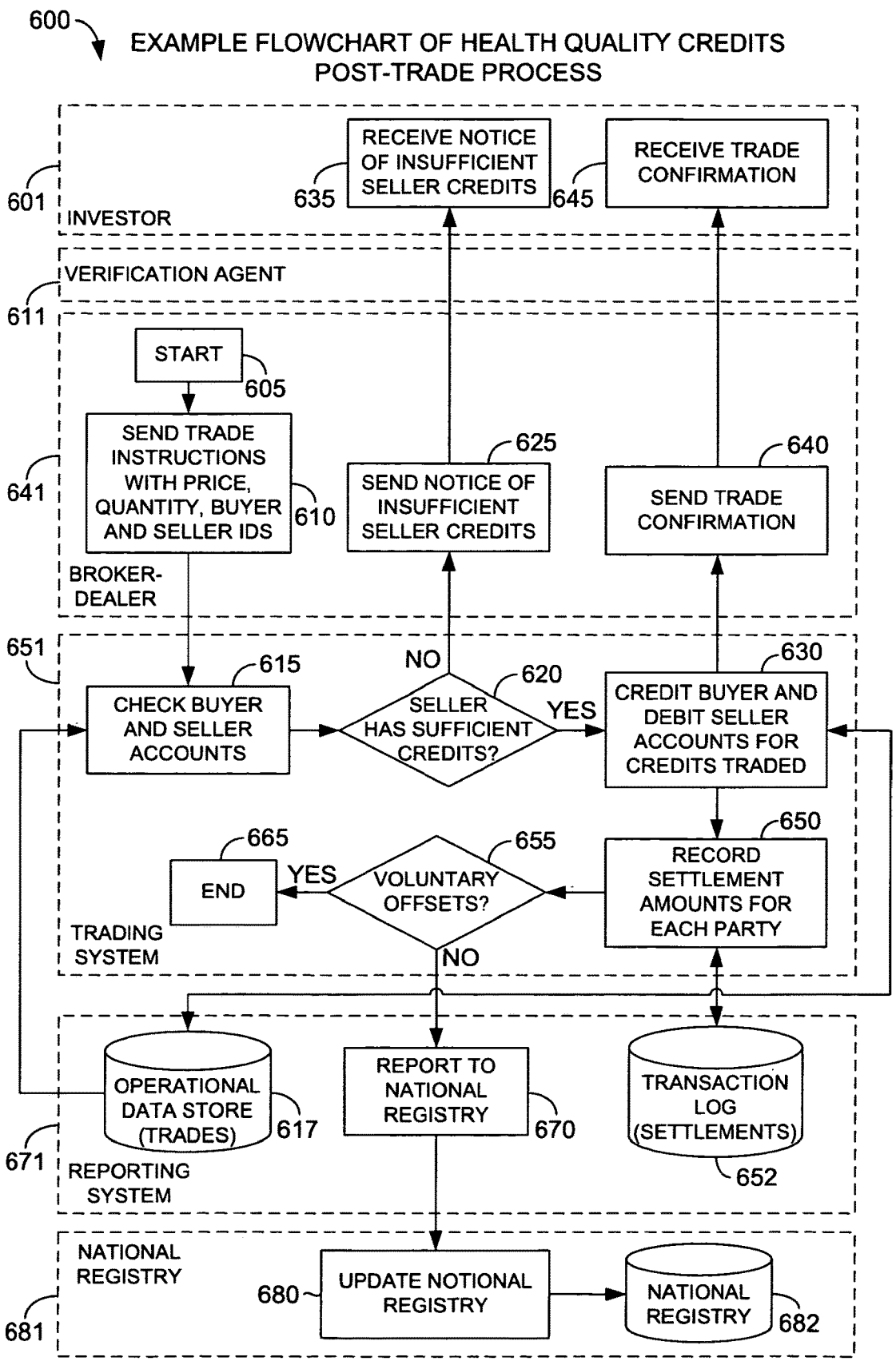
FIG. 6 depicts a flow diagram of a method for handling trade and post trade activity, in accordance with an embodiment of the invention.
Figure 7:
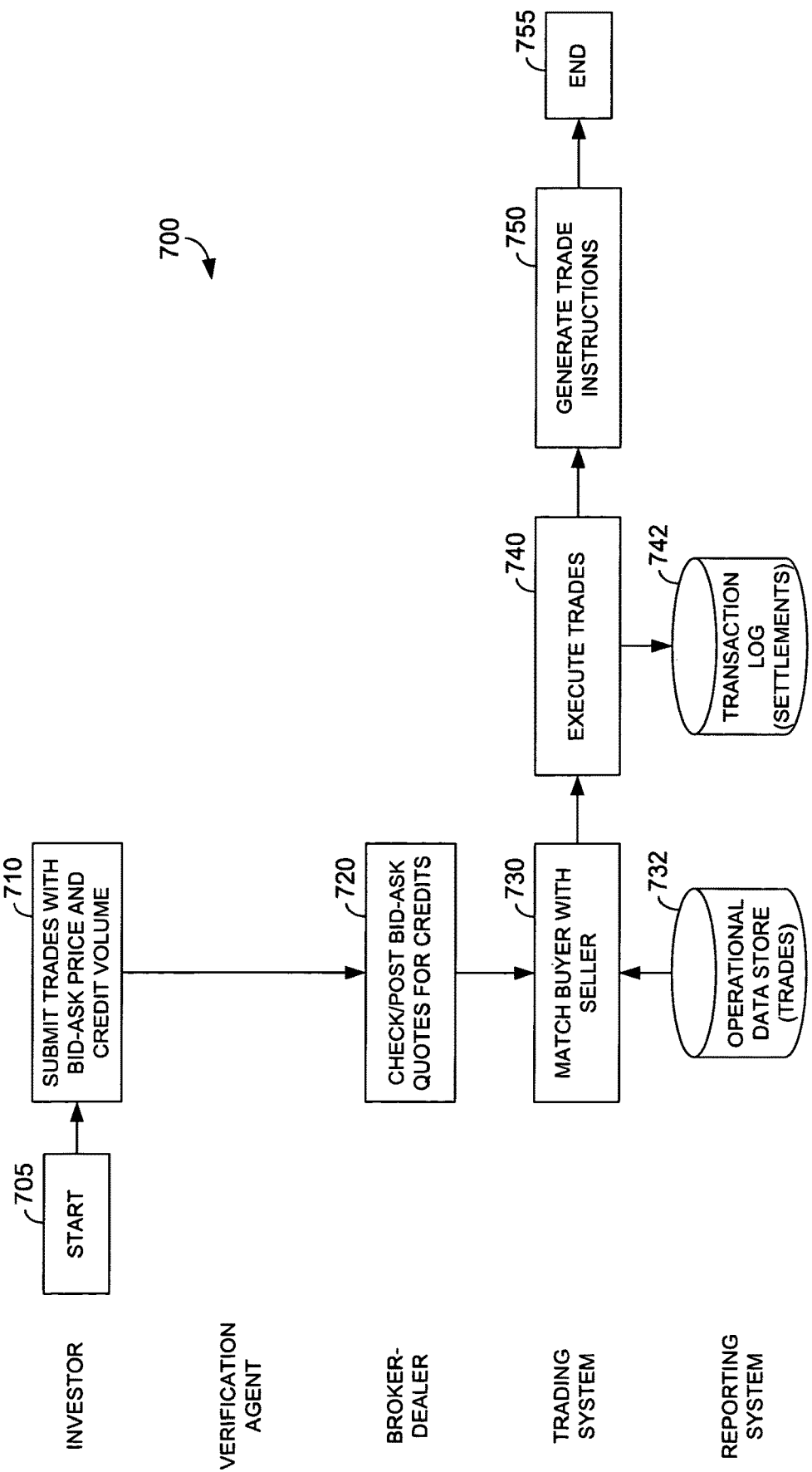
FIG. 7 depicts a flow diagram of a method for trading health quality credits, in accordance with an embodiment of the invention.

Turning to FIG. 7, a flow diagram of a method for trading health quality credits is provided and referred to herein as method 700. The example embodiment of method 700 starts at a step 705 associated with an investor component such as investor 183 or provider-investor 178 of FIGS. 1A and 1B. At a step 710, investor submits one or more trades of health quality credits associated with a bid price or ask price (sometimes referred to as a "bid-ask" price, where the bid represents a price the investor is willing to buy, and the ask represents the price at which the investor is willing to sell) and a credit volume. At a step 720, the submission is received by broker-dealer, such as broker-dealer 177 of FIGS. 1A and 1B. At step 720, broker-dealer component receives a bid quote (price at which credits are being offered on the exchange or posts an ask quote (price at which the investor is asking for the sale of credits). In some embodiments, broker-dealer checks or posts the quote on trading and reporting system 182 of FIGS. 1A and 1B. At a step 730, a buyer of credits and seller of credits are matched in trading system, which may be embodied as trading and reporting system 182. In some embodiments, an account associated with a buyer is matched with an account associated with a seller, such that an amount of credits to be exchanged in a transaction from the seller's account to the buyer's account in return for an agreed-upon value, which may be a market rate, is identified. Operational data store 732, which may be embodied as data store 125, provides trades information to step 730 including market rates for health quality credits. At a step 740, one or more trades are executed between buyer and seller accounts. Trading system stores information about the transaction, such as net settlements information, in a data store at 742, which may be embodied as data store 125. At step 750, trade instructions are generated. In some embodiments, trade instructions include computer instructions for debiting a seller's health quality credit account and crediting a buyer's health quality credit account, including a price, quantity of credits, and buyer and seller IDs, as well as updating registries to reflect new ownership. In some embodiments, trade instructions are generated by broker-dealer or investor and communicated to the trading system. In some embodiments, step 750 progresses to step 605 and 610 or FIG. 6. Thus, at step 755 method 700 ends.

Turning to FIG. 6, a flow diagram is provided of a method for handling trade and post-trade activity, and is referred to herein as method 600. Method 600 starts at step 605 with a broker-dealer 641 (identified as dashed-box 641), which may be embodied as a broker-dealer component 177, of FIGS. 1A and 1B. At a step 610 trade instructions are communicated to trading system 651, which may be embodied as trading system 182. In some embodiments, trade instructions further including information specifying price, health quality credits quantity, and buyer and seller account identification, and in some embodiments further comprise computer instructions for facilitating the trade. At a step 615, trading system 651 checks buyer and seller accounts to determine if the seller account has sufficient credits to complete the trade and if the buyer account has sufficient funds, credits of another credit type, or other value to be exchanged for credits from the seller's account to complete the transaction. In one embodiment, step 615 checks to see that the buyer has established an account that is able to receive health quality credits. In embodiments, at 617 trading system 651 receives trade information from a data store associated with reporting system 671. In some embodiments, trade information includes health quality credits market exchange rates.

Continuing with FIG. 6, at a step 620, method 600 determines whether the seller account has sufficient credits to complete the trade transaction. If the seller's account has insufficient credits, then at step 625, broker-dealer 641 communicates a notice of insufficient seller credits to investor component 601. At step 635, investor 601 receives notice of insufficient seller credits. Returning to step 620, if the seller account has sufficient credits for completing the transaction, then at step 630 the buyer account is credited and the seller account is debited by the credits exchanged. At a step 640, a confirmation of the exchange is received by broker-dealer 641. Broker-dealer 641 communicates the trade confirmation to investor 601. At 645, investor 601 receives confirmation of the trade. In an embodiment, investor component displays a confirmation of the trade to a user through a user interface associated with investor component 601. At a step 650, trading system 651 records settlement accounts for the buyer and seller. In some embodiments, trading system 651 reports settlement information to reporting system 671 at 652. Embodiments of steps at 630, 650, and 652 are further described in connection to FIG. 8.

In some embodiments, at a step 655 a determination is made as to whether the credits traded are voluntary or mandatory. For example, as described below in connection to FIGS. 3 and 4, health quality credits may be part of a mandatory health quality credit exchange or in a voluntary exchange. In some embodiments, health quality credit trading in a mandatory exchange uses a national registry of health quality credits, as described above in connection to FIG. 1A. Accordingly, if at step 655, credits traded are determined to be voluntary, method 600 ends. But if the credits traded are not voluntary (mandatory), then at step 670 reporting system 671 reports information about the transaction to national registry 681. At step 680, national registry 681 receives information about the transaction and updates the national registry at 682. In one embodiment updating the registry includes updating ownership information associated with the traded credits to reflect the ownership of the buyer (buyer-investor) or the buyer's account.

Figure 8:
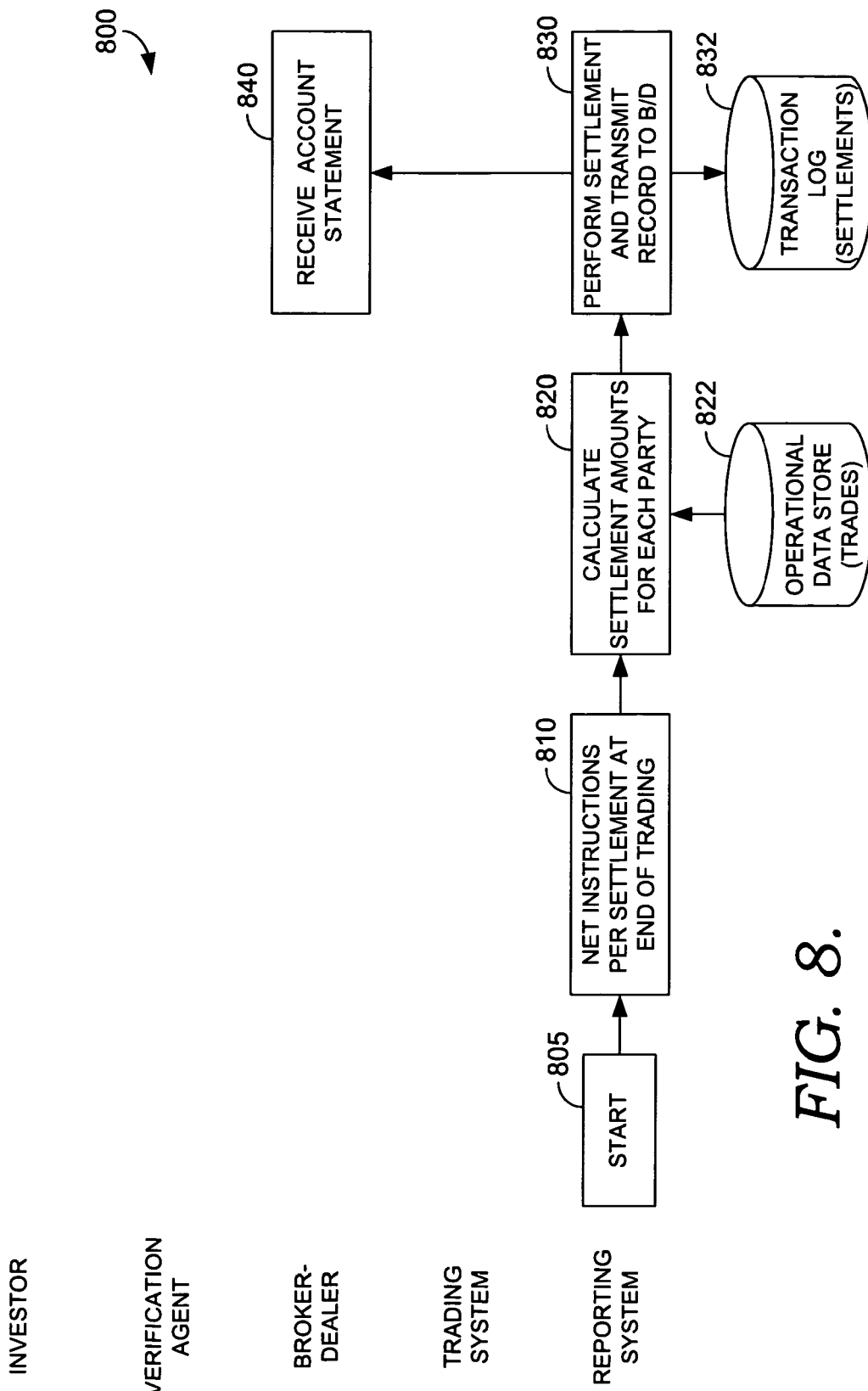
FIG. 8 depicts a flow diagram of a method for netting and determining settlement of trade-transactions, in accordance with an embodiment of the invention.

FIG. 8 depicts a flow diagram of a method for netting and determining settlement of trade-transactions herein referred to as method 800, and which is associated with steps 630, 650, and 652 of method 600 in FIG. 6. The example embodiment of method 800 begins at a step 805 associated with a reporting system. In some embodiments, a trading system has communicated to reporting system settlement information or information associated with a trade. At a step 810, following trading, instructions per settlement transaction are netted. At a step 820, settlement amount for each party's account is determined, based on the netted transactions. In some embodiments, Information associated with the accounts and trades is received at 822 from a data store such as data store 125. At a step, 830, settlement is performed for the buyer and seller accounts and a record of the settlement is recorded into a data store at 832 and communicated to a broker-dealer(s) component associated with the buyer and/or seller. At step 840 a broker-dealer receives an account statement associated with the settlement from the reporting system. In some embodiments, the broker-dealer component integrates the received settlement record into existing information associated with a buyer-investor or seller-investor account, and in some embodiments communicates updated account information to an investor component associated with a buyer-investor or seller-investor (not shown in FIG. 8). In some embodiments, the broker-dealer component or investor component displays the received account statement.

A significant limitation of the prior art is that it lacks investability, in terms of tradable securities; lacks a transparent mechanism for evaluating the underlying assets and liabilities that are pertinent to individual securities' valuations; lacks at least one exchange in which securities can be traded efficiently; and lacks a viable market comprised of a supply of buyers and sellers sufficient to provide attractive liquidity, acceptable volatility, and ready availability of counterparties for a diversity of trades and investment strategies.

But embodiments of our technologies provide for investability by combining methods and systems for offsets trading with the advantages of modern electronic health records systems using mapped, standardized nomenclatures such that ascertaining quality levels and conformity to established target quality standards can be accomplished efficiently for the purpose of issuing health quality offsets. Health Quality Credit Futures, Options, and Spot contracts enable hedging future exposures, and taking 'long' or 'short' positions in health quality credits and health quality credit derivative securities.

In some embodiments, software routines or software agents facilitate synonymic matching and/or ontology mapping among disparate EHR systems, and master-patient-indexing (MPI) or patient-record linkage among patient records in disparate EHR systems, in order to determine universal, standardized nomenclatures and patient outcomes in a plurality of EHR systems. Such embodiments facilitate quickly and efficiently ascertaining quality levels and conformity to established target quality standards by health entities. For example, suppose a health care entity operates several hospitals and at least two hospitals have EHR systems using different synonyms or ontology's. In order to determine total an emission count of total qualifying PACs by the health entity, or to evaluate results of a QDM, JI, or similar project implemented by the health care entity, it might be necessary to map or match the ontology and/or synonyms used by one EHR system to that of the other, or convert both to a standardized or universal nomenclature which is used for emissions counting, emission reduction by applying health quality credits, or reporting. Additional information and example embodiments of synonymic matching, which may be applied to embodiments described herein, is provided in U.S. patent application Ser. No. 13/569,781, titled "Synonym Discovery", filed on Aug. 8, 2012, which is herein incorporated by reference in its entirety. Similarly, additional information and example embodiments of ontology mapping, which may be applied to embodiments described herein, is provided in U.S. Provisional Application No. 61/544,919, titled "Ontology Mapper", filed Oct. 7, 2011, which is hereby expressly incorporated by reference in its entirety. Finally, additional information and example embodiments of patient record linkage, which may be applied to embodiments described herein, is provided in U.S. Provisional Application No. 61/641,097, titled "System and Method for Record Linkage", filed May 1, 2012, which is hereby expressly incorporated by reference in its entirety.

With continuing reference to the methods 600, 700, and 800, in some embodiments, entities with surplus health quality credits can sell them to entities with quantified emission limitation and reduction commitments. In these embodiments, in terms of assets, if a health quality emitting entity can under use its initial allowance cap by better quality and efficiency, besting the target limits, it can sell its surplus health quality credits on the market. In terms of liabilities, if an entity faces high costs to reduce its health quality emissions and can buy credits/allowances more cheaply in the open market, or if it is ineffective in reducing emissions and exceeds its cap, it will buy extra credits in the market. For example, it may be prohibitively expensive or impractical in terms of available resources for an 85-bed hospital in a rural area to implement certain programs that qualify as a reduction in emissions. So such a hospital may want to purchase health quality credits at least initially, until it can accord to implement the qualifying programs. Similarly, other health care entities may be better able to better handle changes in patient population, regulations, or other changes to the health care industry, which may increase financial constraints on the entity by having the option to purchase health quality credits.

Turning to FIG. 5, an embodiment of a method for retiring health quality credits is provided and referred to herein as method 500. At a step 505, an investor component, such as provider-investor 178 submits trades of credits for retirement. In embodiments, retired credits are applied to reduce emission and thus no longer available for trading on a health quality exchange. At a step 510, broker-dealer enters an order to retire the specified credits, based on the trades of credits submitted at step 505. At a step 515, the account associated with the broker-dealer entered order is checked to determine if the account has sufficient credits for retirement. At a step 520, if the account does not have sufficient credits, then at step 525 a notification of insufficient credits is sent to broker-dealer component. In some embodiments, a trading system sends the notification to broker-dealer component. At step 535, the notification of insufficient credits is received by broker-dealer component.

Returning to step 520, if the broker-dealer account has sufficient credits for completing the credit-retirement order, then at a step 530, the broker-dealer account is debited by the amount of credits to be retired. At a step 540, specific credits are designated as retired. In some embodiments, a credit identifier associated with each credit to be retired is annotated to indicate that the credit is retired. At a step 550, a confirmation report of the credit retirement is sent to broker-dealer, and at step 560, the confirmation is received by broker dealer. In one embodiment, an account at the broker-dealer associated with the investor component is updated to reflect the retired credits. In one embodiment, a confirmation of the credit retirement is sent to the investor component.

In some embodiments, emissions trading is available to health care entities (such as, for example, provider individuals, institutions, and health plans) that, despite their best efforts, maintain or increase their year-over-year emissions of controlled health quality indices for which quantitative target limits (annual emission 'caps') have been established, either voluntarily or by government regulation or both. In embodiments, a health quality index maybe considered a 'synthetic', composite measure whose composition and methods of calculation and re-balancing and re-calculation are established by a national registry, and/or by the health quality exchange(s), and/or by private firms who create proprietary indices, similar to equities. Entities can meet their health quality emission caps by purchasing health quality emission reductions from a financial Health Quality Exchange (HQX™); by over-the-counter (OTC) bilateral trades with other health care provider entities directly; or from 'Joint Implementation' (JI) or Quality Development Mechanism (QDM) projects that reduce health quality emissions. In some embodiments of the latter case, only 'Certified Emission Reductions' (CER) credits of QDM projects that are accredited by an authorized 'Designated Operational Entity' (DOE) may be bought and sold in this manner.

The QDM is an arrangement that allows out-performing entities with a net surplus of health quality credits to invest in projects that reduce emissions in underperforming entities as an alternative to, or as a supplement to, additional incremental health quality emission reductions in their own entities. In some scenarios, these "health quality projects" may first provide net "additionality," i.e., that the net reduction would not have occurred without the additional incentive provided by emission reduction credits available under the QDM investment. One QDM's purpose is to allow net health quality emissions to be reduced at a lower overall cost by financing emissions reduction projects in underperforming entities. Theoretically, since the QDM is an alternative to intra-system endogenous health quality emission reductions, a perfect QDM would produce no more and no less health quality emission reductions than without use of the QDM.

In some embodiments under the QDM, flexible mechanisms for trading emission reductions credits can be allowed, including verified emissions trading using Certified Emission Reduction (CER) credits that allow outperforming entities to find emissions reduction activities in underperforming entities as an alternative to intra-system endogenous health quality emission reductions.

Another embodiment using an approach called "Joint Implementation" (JI) applies in transitional entities (such as entities that have implemented Health Information Technologies including computerized physician order entry (CPOE) and decision support, but which have not fully deployed it to achieve HIMSS Level 6 or higher.) Under some embodiments using a JI scheme, projects produce health quality Emission Reduction Units (ERU), which are valid for meeting mandated health quality emissions reduction obligations. CERs and ERUs are generally bought from project developers by health plans or health provider entities, but may also be exchange-traded.

In some embodiments, projects that qualify for offset credit must be verified or validated to rigorous standards for validation of QDM projects by "Designated Operational Entities" (DOE) to ensure "additionality," along with documentation of the measurement and verification methodology applied, as outlined in the project development documentation.

In some embodiments including those having mandatory markets, each entity that participates in a mandatory health quality emission reduction framework and health quality emissions trading scheme maintains their emission allowances or "health quality credits" on the behalf of companies and the government in an electronic account known as a national registry. Various entities are also joined by the registry of the QDM, which holds health quality credits generated by QDM projects on behalf of project sponsors. In embodiments where there are voluntary markets, voluntary registries may also be used. In some embodiments of both mandatory voluntary markets, as a credit is "retired," as discussed in connection to FIG. 5, the registries are updated accordingly. In some embodiments computer interfaces may be used by various national registries to supplement and/or in place the current paper and facsimile system.

Figure 3:
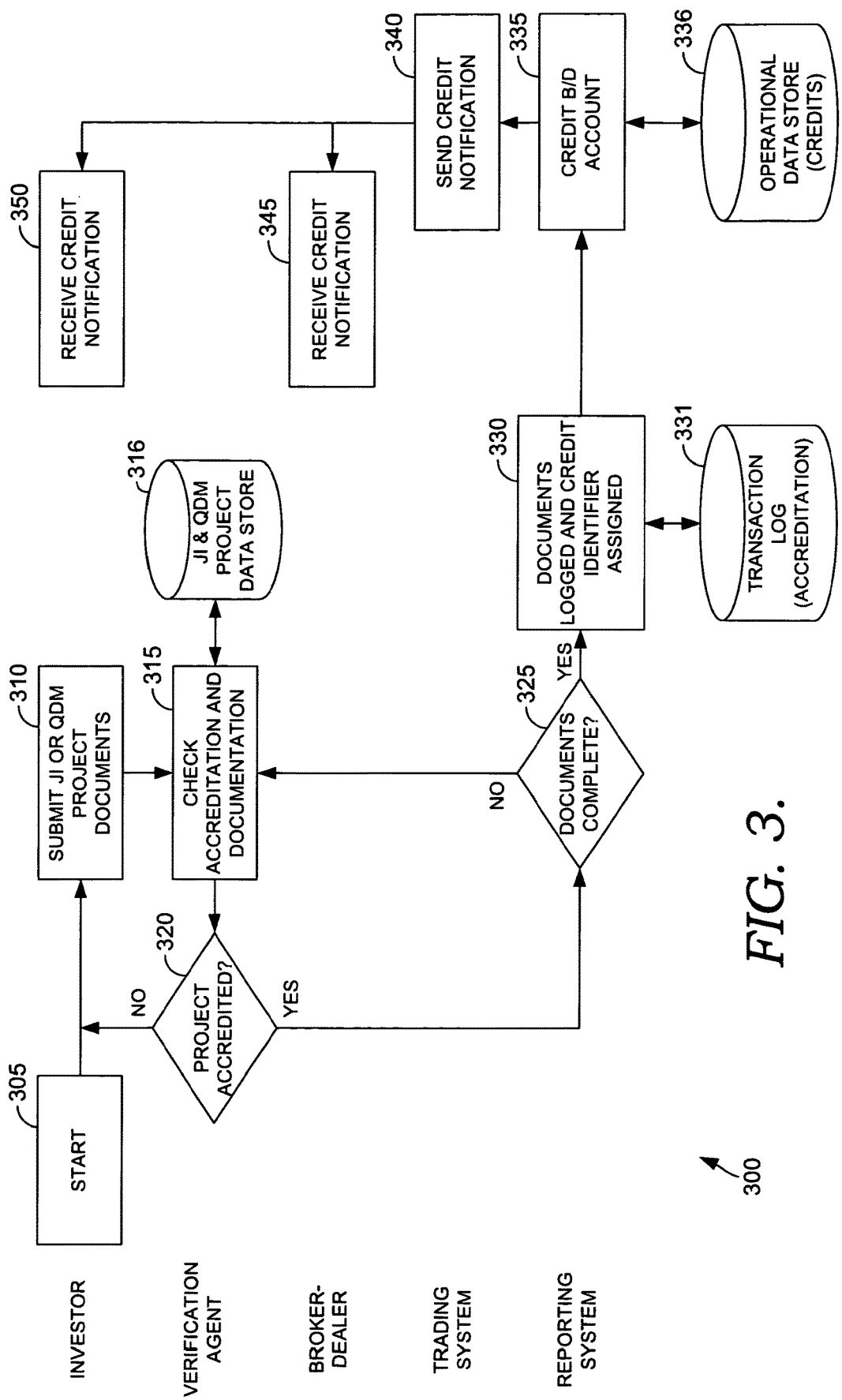
FIG. 3 depicts a flow diagram of a method for registering voluntary offsets, in accordance with an embodiment of the invention.

FIGS. 3 and 4 depict flow diagrams of methods for registering voluntary offsets or mandatory offsets, respectively. Turning first to FIG. 3, a method 300 is provided of an embodiment for registering a voluntary offset that starts at step 305 with an investor component, such as investor 178 or 183. At a step 310, investor component submits JI or QDM project information, such as project documentation, to a verification agent, such as verification agent 185. At a step 315, verification agent checks accreditation and documentation information associated with the submitted project documents. In embodiments, verification agent receives JI and/or QDM project information at 316 from a data store, such as data store 125. At step 320, verification agent determines if the project is accredited based on the information submitted by investor and the QDM or JI information received from the data store at 316. If the project is not accredited, then method 300 returns to step 310. In some embodiments (not shown) method 300 ends or suspends until an investor submits qualifying JI or QDM project information at 310. If at step 320 the project is accredited, then at step 325 reporting system, such as reporting system 182, determines if the submitted information is complete. If incomplete, then method 300 returns to step 315. In some embodiments, if the information is incomplete, method 300 returns to step 310, where the investor may resubmit complete project information, and in some embodiments, method 300 notifies investor component that the project documentation is incomplete. In some embodiments, method 300 terminates at step 325, if the documentation is incomplete, or method 300 is suspended until complete project information is submitted and accreditation confirmed.

At a step 330, completed and accredited project information is recorded in a data store at 331, and a credit identifier is assigned to submitted project and also recorded at 331. In one embodiment, the credit identifier includes a code or number that uniquely identifies a credit (or credits) and associates the credit(s) with the project. In one embodiment the investor or entity submitting the project documentation is designated as an owner of the credit, and the ownership is associated with the credit identifier. At a step 335, a broker-dealer account is credited with the newly registered credit, which may be identified by the credit identifier. At step 336, the updated account information, which now includes the newly registered credit, is stored in a data store, such as data store 125. At step 340, a notification is sent from trading system to the investor component and broker-dealer component. Thus at step 345 the credit notification is received by the broker-dealer component, and at step 350 the credit notification is received by the broker component. In some embodiments, notification may be provided to only the broker-dealer or only the investor. In some embodiments, notification is displayed on a user interface associated with the broker-dealer component or investor-component.

Turning now to FIG. 4, a method 400 is provided of an embodiment for registering a mandatory or regulatory offset that starts at step 405 with an investor component 401, such as investor 178 or 183 of FIGS. 1A and 1B. At a step 410, it is determined whether a credit to be registered is a new or existing, but unregistered credit. If the credit is new, then at step 420, verification agent 411 verifies project accreditation and credit status. At step 430, project information such as project certification documents are communicated to reporting system at step 425. Returning to step 410, if the credit to be registered is an existing credit, then at step 415, investor component submits or provides project information, such as JI or QDM project documentation or verification. Because in this step the project is already verified, method 400 proceeds to reporting system 471 at step 425. At step 425 a determination is made as to whether the JI or QDM project is accredited, based on the submitted information. If not, method 400 proceeds to step 430, where project certification information may be provided by verification agent 411. In some embodiments, investor component 401 is notified that the project is determined to be unaccredited based on submitted information.

At a step 435 a credit identifier is assigned to associate an identifiable credit (or credits) with the project. In one embodiment, the credit identifier includes a code or number that uniquely identifies a credit (or credits) and associates the credit(s) with the project. In one embodiment the investor or entity submitting the project documentation is designated as an owner of the credit, and the ownership is associated with the credit identifier. At a step 450, an update to broker-dealer account is generated to include information about the newly registered credit, which may be identified by the credit identifier. At a step 452, a data store (such as data store 125) storing credit registration and transfer information receives a record of the newly registered credit and in some embodiments the associated ownership of the credit. In some embodiments, following step 450, a notification of the credits update is sent from reporting system 471 to investor component 401 or broker-dealer component 441.

At step 440, a notification of the credits update sent from reporting system 471 is received at a broker-dealer component. And at step 490, a notification of the credits update sent from reporting system 471 is received at investor component 401. In some embodiments, notification may be provided to only the broker-dealer or only the investor. In some embodiments, notification is displayed on a user interface associated with the broker-dealer component or investor component.

Returning to step 450, following generation of a credits update to the broker-dealer account associated with the submitted project, national registry is updated to reflect the new or transferred credit. Thus at step 480, a determination is made as to whether the credit is new or existing. In one embodiment, information determined at step 410 is accessed and used to evaluate the decision at step 480. In one embodiment, an identifier associated with the credit indicates historical information about the credit, such as its creation date, which is useable to evaluate the decision at step 480. If it is determined that the credit is new, then at step 484, the new credit is registered and stored in the national registry data store at 482. In one embodiment, the new credit is assigned a registration number which is recorded in the national registry. In one embodiment, ownership of the credit is also recorded, and in one embodiment an investor-account associated with the credit is recorded. Returning to step 480, if it is determined that the credit is an existing credit, then at step 486 the credit is transferred and the registration recorded in the national registry at step 482. In one embodiment ownership or credit type is updated in the registry to reflect the transfer.

With reference to step 315 of method 300, in some embodiments, the standards and certification schemes for the voluntary health quality market can be divided into two broad categories. First, there are those whose purpose is to certify the quality of the offsets and the projects that generate them. These include the Voluntary Health Quality Standard, JCAHO Core Measures, CMS, AHRQ PSnet National Patient Safety Goals (NPSGs), Leapfrog Standards, and other offset-related protocols.

With reference to methods 300, 400, and 700 generally, a second set of standards, in these embodiments, focuses more on certifying offset sellers, products, services, and/or the claims of health quality neutrality being made by individuals and institutions.

The various embodiments using voluntary reduction schemes or "health quality markets" use different formal standards (also called protocols) for quantification of offsets, now being developed based on collaboration between emitters, regulators, health quality analysts, and project developers. Some of these standards impose the same "additionality" requirement as in the QDM, while in some embodiments, a standards includes its own requirements. For example, by way of analogy, in carbon emissions, the ISO 14064 standard specifies its own requirements.

In an embodiment, generally voluntary health quality markets include all health quality offset trades that are not required by state or federal regulation. For example, voluntary market transactions include: the purchase of health quality credits by individuals or institutions at a retail OTC level to offset their emissions; the purchase of credits directly from project developers for retirement or resale; and the donation to health quality emissions reduction projects by corporations in exchange for credits. In some embodiments, at the broadest level, the voluntary health quality markets can be divided into two main segments: the voluntary, but legally binding, cap-and-trade system that is the Health Quality Exchange (HQX™); and the broader, non-binding, over-the-counter (OTC) offset market. CERs and ERUs derived from the mandatory QDM and JI programs can also be sold on the voluntary markets.

Although typically less than the expected trading volume of embodiments using mandated regulatory health quality credits, embodiments using voluntary markets are significant in that they represent an active and growing demand by businesses and individuals for health quality offset trading. In one embodiment, a voluntary market in North America might reside mostly in the legally nonbinding over-the-counter (OTC) market, while a smaller portion might be traded under the voluntary, legally-binding cap-and-trade Health Quality Exchange (HQX™) mechanism.

By way of background, from an economic or market perspective, there is a distinction between a mandatory market and a voluntary market. Typically both markets could deal with health quality emission certificates of some form, but in the mandatory market, it is contemplated that strict rules would be applied for project approval and accounting, i.e., "verification & validation." A voluntary market might provide entities with different options to acquire health quality emissions reductions, and include solutions comparable to those developed for a mandatory market.

The quality of health quality offsets is, and will likely continue to be, an important issue for both buyers and sellers in embodiments using either mandatory markets or voluntary markets, and will help determine how these markets grow. In these embodiments, offsets quality also influences the price of health quality credits in the market. In some embodiments, issues that determine quality of offsets in this market include additionality (would the reductions have happened anyway with or without the offset purchases), third-party certification and verification, standards, and avoidance of double-counting and double-selling of offset credits (i.e., use of registries).

In some embodiments, health quality emissions reduction credits (or offsets) may be granted annually to health care entities, based on the type and size of the particular entity. By analogy, the granting of health quality emissions reduction credits may be understood by looking at the granting of fishing quotas or carbon emissions credits. (However, the manner that a credit is determined and applied in a health care context is obviously different. Similarly, the manner in which a health quality credit is bought, sold, traded, and monitored is different since the health care industry is different from the fishing industry.) In some embodiments a governmental entity such as a state or federal agency, a public-sector entity, or NGO (nongovernmental organization) issues health quality credits and grants the credits to each health care industry. In some embodiment the health quality offset credit further comprises a health quality credit issued by the Health Quality Exchange (HQX™). And in some embodiments, the health quality offset credit further comprises a Certified Emission Reduction (CER) or Emission Reduction Unit (ERU) established under a standard associated with a health quality exchange. In some embodiments, health quality credits may be funded by existing fines imposed upon health care entities for failing to meet minimum conformity standards.

As described above in connection to FIG. 5, in embodiments, a health quality credit may be retired by applying the credit to health quality emissions. In some embodiments, one health quality credit or offset may offset (or be equal in value to) one PAC (potentially avoidable complication), one PAM (potentially avoidable mortality), or one QCM (qualified core measure unit), and in some embodiments a plurality of different credit-types exist, such that each is associated with a particular emission type. In some embodiments, a qualified core measure unit (QCM) may be used, which may be related to at least one QDM or JI, and which represents a set or unit measure of potentially avoidable patient outcomes. For example, one QCM might be "100 diabetic patients deviating 3 percentage points above target HbA1c". In other words, for some embodiments, while the quality levels are specified in ratio or 'relative' or 'percentage' terms, the credits are issued and exchanged in 'absolute' numbers that deviate by a specified amount from the target. This provides an advantage of scaling, so that credit issuance will scale with patient population size and services volume.

For example, in one embodiment, a PAM credit may be applied to reduce an emission count due to a potentially avoidable mortality. Similarly, a PAC credit may be applied to reduce an emission count due to a potentially avoidable complication. Moreover, in some embodiments a PAM-associated credit may be applied to offset a PAC-related emission, or may be converted to an equivalent number of shares of PAC credits. Still further, in some embodiments, health quality credits (sometimes referred to as health quality offset credits or shares) may be associated with specific categories of condition. For example, a health care entity may be granted an annual quota of a plurality of different types of health quality shares including certain types of PACs such as a first type of offset credit associated with instances of hospital acquired pneumonia and a second type of offset credit associated with instances of hospital acquired bedsores (decubitus). Again in some embodiments, credits may have a hierarchical value enabling some credits (such as credits for more severe PACs) to be applied (and thereby retired) to less severe PACs. In some embodiments, credits of different types may be converted to other credit types or exchanged for health quality credits of a different type. This might occur where a health care entity performs above average in a particular area associated with a particular type of credit, or invests in projects to earn a particular credit type, thereby acquiring a surplus of that credit type, but fails to meet conformity standards in another particular area associated with a different credit type. In this example, the health care entity will likely want to exchange the credit type for which it has a surplus for credits to be applied to the area in which it is failing to meet conformity standards. In another example, suppose a particular long-term health care entity treating stroke patients has 30% of its patients on ventilators. If the entity is receiving a capped DRG-based payment (diagnosis-related group-based payment) per patient, then this might represent a high potential for financial loss, because the cost of caring for a patient on a ventilator for a very long period will likely exceed the DRG-based payment. In this scenario, the entity would consider purchasing health quality offset shares applicable to this type of service. If the entity received a quota of shares that included shares related to pediatric orthopedics, for example, the entity would likely sell or exchange those share types for the appropriate share type to apply and thereby reduce its liabilities.

In some embodiments, health quality emissions may be classified into grades or levels, such that each level has an emission value or count associated with it. For example, for emissions related to preventable bedsores, outcomes associated with patient treatment might range from good, bad, very bad, and reprehensible (a high percentage of patients acquired bedsores). In these embodiments the amount of credits needed to offset a unit count in a particular grade or level can vary based on the level. For example, a single "emission" or emission count in a "bad" grade, may require only one credit (of the appropriate credit type) to reduce or cancel out the emission, but an emission count in a "very bad" grade may require two credits (of the appropriate credit type) to reduce or cancel out the emission. In some embodiments, the determination of emission levels is based on existing health care quality of care standards, for example, joint-commission standards, Institute of Medicine, and Medicare standards used to assess care quality. In some embodiments a heath care entity tracks and reports emission counts, and in some embodiments, standardized nomenclatures are used to facilitate an automated identification of emission types or retirement of credits to offset those emission types. In some embodiments, this is facilitated by software agents or software routines. Similarly, in some embodiments, a software agent or routine evaluates a health care entity's EHR system information for patients outcomes over a time-period, and, based on existing health care standards such as Medicare standards, identifies the instances where the health care entity likely failed to conform to the standard. In some embodiments, the agent or routine counts these instances and equates the count to an emission count, which may be associated with an emission level or grade. In some embodiments thresholds may be set for exchangeable credits based on patient treatment outcome, wherein the thresholds establish the number and type of credits needed to offset an emission count, for each emission grade or level.

As further described above and in connection to FIGS. 3 and 4, in some embodiments credits may be earned by investing in qualifying programs that reduce emissions. In some embodiments, credits may be awarded to the health care entity upon the submission or undertaking of the project, so that a particular entity in need of credits for a given year can begin a qualifying project and receive credits to apply that year. But in these embodiments, it is desirable to implement a claw-back mechanism such that the undertaken project (such as a JI or QDM project) is evaluated by a monitoring authority, and if the project fails to satisfy the project requirements, the previously awarded credits are clawed (or taken) back. In some embodiments, the monitoring and evaluating is facilitated by one or more software agents or software routine, applying software services of stack 121. In an embodiment, the software agent or routine evaluates the project results, which might include for example, examining the electronic health records of the entity that implemented the project, for changes in the record indicative of successful outcome of the program objectives. For example, in a JI or QDM project associated with reducing patient obesity by providing nutrition awareness to patients of low income, a software agent might examine the EHR system of the health care entity and count the average weight change of patients in the program, the number of hours of instructional awareness provided by the health care entity, reductions in the numbers of complications resulting from obesity, or similar metrics for evaluating the EHR system for changes indicative of successful implementation of the program. Further, in some embodiments, the agent or routine reports the result of the evaluation, including instances indicating potential failure to meet project standards or criteria to a reviewing authority.

Turning now to FIGS. 9 and 10, flow diagrams are provided for method 900 of reporting a transaction and a method 1000 for market data reporting, respectively. Turning first to method 900, at a step 905, method 900 starts at broker-dealer, such as broker-dealer component 177 of FIGS. 1A and 1B. At a step 910, broker-dealer component requests an account statement from a reporting system, such as reporting system 182. At a step 920, reporting system receives the request and determines settlement amounts for each party (buyer and seller) for transactions, based on trade and settlement information. In some embodiments, settlements have already been determined, and in some embodiments only outstanding. undetermined settlements are determined in step 920. At step 922 trades information is provided and at step 924 settlements information is provided to reporting system at step 920. In some embodiments, the data stores associated with steps 922 and 924 are the same data store, such as data store 125. At step 930, account information is generated. In some embodiments, the account information includes account settlement information, transaction history, and position information. At a step 940, broker-dealer receives the account information. In some embodiments, broker-dealer receives the account information in the form of an account statement. In some embodiments, broker-dealer provides the account statement to investor-component (not shown). In some embodiments, a user interface associated with the broker-dealer or investor displays the account statement.

FIG. 10 shows an embodiment of a method for reporting market data and begins at a step 1005 associated with a reporting system, such as reporting system 182 of FIGS. 1A and 1B. At a step 1010, transactions occurring over a reporting period, which may be hourly, daily, weekly, monthly, or other span of time, are aggregated. In an embodiment, records of trade transactions or trade information are received from a data store at 1012. In one embodiment, transaction events are compiled and identifying information indicating specific buyer-accounts, seller-accounts or information deemed private is removed. At a step 1020, bid-ask prices, completed-transaction prices, and volumes for credits trades information is published. In one embodiment, this information is published into a database, stored at 1022 on a data store such as data store 125, and accessible to broker-dealer component 177 or investor components 178 and 183. In one embodiment, the published information is accessible over a software application with a user interface, such as a Web browser, associated with broker-dealer component 177 or investor components 178 and 183. Thus at step 1030, broker-dealer accesses published reports and transaction history.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

With reference to FIGS. 2 through 10, additional example embodiments include:

A method of accounting for health quality offset credits established in one or more offset markets, the method comprising: registering a health quality offset credit to an owner thereof; assigning a unique identifier to the health quality offset credit; receiving instructions of a pending trade of the health quality offset credit between a buyer and a seller; if the seller has an amount of health quality offset credits sufficient to complete the trade, adjusting buyer and seller accounts with corresponding credits and debits; otherwise, providing a notification of an insufficient health quality offset credits to carry out the trade.

In an embodiment, the health quality offset credit further comprises a potentially avoidable complication (PAC) offset, a potentially avoidable mortality (PAM) credit, or a qualified core measure (QCM) credit. In an embodiment, the health quality offset credit further comprises a CFI health quality credit issued by the Health Quality Exchange (HQX™) In an embodiment, the health quality offset credit further comprises a Certified Emission Reduction (CER) or Emission Reduction Unit (ERU) compliant under a Health Quality Protocol.

In an embodiment of this method, the health quality offset credit is a verified offset, and in another embodiment the verified health quality offset credit has been verified using a verification standard compliant under the Health Quality Protocol.

Some embodiments of this method further comprise crediting a client account with the health quality offset credit.

In an embodiment, the environment offset credit is verified under a voluntary offset scheme, and in another embodiment, the health quality offset credit comprises a health quality offset verified using an accredited standard that has been promulgated by an authorized public-sector regulatory body or private-sector standards organization.

Some embodiments of this method further comprise registering a plurality of health quality offsets to respective owners thereof, wherein two or more of the health quality offsets have been verified under different voluntary standards.

Some embodiments of this method further comprise registering a plurality of health quality offset credits to respective owners thereof, wherein two or more of the health quality offset credits are traded in at least two different offset markets.

In an embodiment, the trade notification comprises price and quantity information, and in an embodiment, the health quality offset credit is a government-regulated offset credit, and wherein the method further comprises providing an update to one or more associated national offset registries.

Additional example embodiments further include: a method of trading and accounting for health quality offset credits established in two or more different offset markets, the method comprising: registering, in a database, a plurality of health quality offset credits established in the two or more different offset markets; assigning each of said plurality of health quality offset credits with a unique identifier; receiving a bid or ask quote for one of the plurality of health quality offsets established in one of the two or more different offset markets; matching a buyer with a seller of said one of the plurality of health quality offset credits based, at least in part, on the received bid or ask quote; if the seller has an amount of health quality offset credits sufficient for a trade, executing a trade of said one of the plurality of health quality offset credits between the buyer and the seller; and otherwise, providing a notification of insufficient health quality offset credits to carry out the trade to at least the seller.

Some embodiments further comprise entering an offsetting credit and debit of the traded health quality offset credit to respective client accounts maintained in the database; some embodiments further comprise providing a notification of the traded health quality offset credit to the buyer and seller; some embodiments further comprise providing a notification of the traded health quality offset credit to a national registry associated with said one of the plurality of health quality offset credits; and some embodiments further comprise executing, between at least one different buyer or seller, multiple trades of different health quality offset credits verified under different standards.

In an embodiment, providing a notification comprises providing an electronic notification to the associated national registry via a computer network.

In some embodiments, the method further comprises computing an offset credit amount and cash value to be applied to the executed trade. In some embodiments, the method further comprises performing a clearing and netting operation to consolidate and report trades between at least a first buyer-seller pair during a predetermined time period. In some embodiments, the method further comprises converting a physical offset certificate associated with the traded health quality offset credit into a book-entry form maintained in the database. In some embodiments, the method further comprises storing, in the database, a record of current and historical offset credit positions and prices for one or more clients.

In some embodiments, the method further comprises providing client position statements relating to one or more of the plurality of health quality offset credits established in the two or more different offset markets. And In some embodiments, the method further comprises confirming that related offset documentation is complete, and scanning said completed related offset documentation to said database, prior to said executing a trade.

In an embodiment, at least one of the plurality of health quality offset credits is established under a regulated mandatory scheme. And in an embodiment at least one of the plurality of health quality offset credits is established under a voluntary offset scheme.

Additional example embodiments further include: a computer-implemented platform useful in accounting for health quality offset credit trades made in two or more offset markets, the trading platform comprising: one or more processors; a memory operatively coupled to the one or more processors, said memory comprising a structured database therein configured to store information relating to one or more health quality offset credits established in the two or more different offset markets; an interface to the one or more processors configured to forward a bid and/or ask quote for one of the two or more health quality offset credits to said one or more processors, said one or more processors matching a buyer with a seller of said one of the two or more health quality offset credits based, at least in part, on the received bid or ask quote, said one of the two or more health quality offset credits being established in one of the two or more different offset markets; wherein, if the seller has an amount of health quality offset credits sufficient for the trade, the one or more processors generates a signal that indicates, to at least the seller, that sufficient health quality offsets are available to carry out a trade of said one of the two or more health quality offset credits between the buyer and the seller, and wherein, if the seller does not have an amount of health quality offset credits sufficient for the trade, the one or more processors generates a signal that indicates, to at least the seller, that insufficient health quality offsets are available to carry out the trade.

In an embodiment, the one or more processors executes a trade of said one of the two or more health quality offset credits between the buyer and the seller if the seller has an amount of health quality offset credits sufficient for the trade.

In an embodiment, the computer-implemented platform includes instructions to credit a client account, in the structured database, with a traded health quality offset credit.

In an embodiment, the computer-implemented platform includes instructions to compute an offset credit amount and cash value to be applied to the executed trade.

In an embodiment, the computer-implemented platform includes instructions to enter an offsetting credit and debit of the traded health quality offset credit into respective client accounts maintained in the structured database.

In an embodiment, the computer-implemented platform includes instructions to provide a notification of the traded health quality offset credit to the buyer and seller via a network.

In an embodiment, the computer-implemented platform includes instructions to provide, via a computer network, an electronic notification of the traded health quality offset credit to a national registry associated with a traded health quality offset credit.

In an embodiment, the computer-implemented platform includes instructions to perform a clearing and netting operation to consolidate and report trades between at least a first buyer-seller pair during a predetermined time period.

In an embodiment, the computer-implemented platform includes instructions to store information representing a physical offset certificate associated with a traded health quality offset credit into a book-entry form maintained in the structured database.

In an embodiment, the computer-implemented platform includes instructions to register, in the structured database, a health quality offset credit to an owner thereof and to assign a unique identifier to the health quality offset credit.

In an embodiment, the unique identifier comprises either a CUSIP or an ISIN identification number.

In an embodiment, the computer-implemented platform includes instructions to execute, between at least one different buyer or seller, multiple trades of different health quality offset credits verified under different standards.

In an embodiment, the structured database stores information relating to a plurality of health quality offset credits established in the two or more different offset markets and established under two or more voluntary offset schemes.

In an embodiment, the computer-implemented platform includes instructions to provide client position statements relating to one or more of the plurality of health quality offset credits established in the two or more different offset markets.

Additional example embodiments further include: a method of converting a health quality offset credit, the method comprising: retiring an offset credit verified under a first verification standard; verifying a new offset credit under a second verification standard, said new offset credit being essentially equivalent to the first offset credit at least in terms of representing a desired reduction in emissions; and thereafter, registering the new offset credit in a registry to a owner thereof. In an embodiment, the first and second verification standards comprise different voluntary health quality standards.

The invention claimed is:

1. A system for improving health care provided by a health care entity using health quality credit exchange and electronic health record (EHR) systems, comprising:
one or more processors configured to:
receive an order to retire one or more health care quality credits, wherein the order is associated with a health care entity;
access a health care quality credit account associated with the health care entity and determine if a health care quality credit account associated with the health care entity has sufficient health quality offset credits to fulfill the order to retire one or more health care quality credits;
if there are a sufficient number of health quality offset credits in the health care quality credit account, apply a set of health quality offset credits to the order;
retire the set of health quality offset credits by annotating a unique credit identifier associated with each health quality offset credit of the set of health quality offset credits as retired; and
reduce a number of health quality offset credits in the health care quality credit account, wherein a retired health quality offset credit becomes no longer available for trading on a health quality exchange.

2. The system of claim 1, wherein the health quality offset credit is received from a health quality credits exchange in return for money.

3. The system of claim 2, wherein a registration is associated with the received health quality offset credit, and wherein the registration is updated to reflect ownership by the health care entity.

4. The system of claim 1, wherein the health quality offset credit is received from an allotment of health quality offset credits granted to the health care entity over a time period.

5. The system of claim 1, wherein the health quality offset credit is received based on a qualifying event undertaken by the health care entity.

6. The system of claim 1, wherein an emission value associated with the emission count is based on a PAC or PAM associated with the health care entity.

7. The system of claim 1, wherein identification information is associated with each health quality offset credit of the set of health quality offset credits, and further comprising updating the identification information to indicate that each health quality offset credit of the set of health quality offset credits is retired.

8. A method for improving health care by a health care provider using health quality credit exchange and electronic health record (EHR) systems, the method comprising:
accessing an EHR system, associated with the health care provider, that stores patient health care information including patient-treatment outcomes;
determining an emission level for the health care provider; and
retiring a first credit based on an emission level offset value associated with one or more health quality credits and a reduction amount wherein the reduction amount is determined based on the determined emission level for the health care provider.

9. The method of claim 8, wherein the method further comprises maintaining an account of health quality credits, the account associated with the health care provider and depositing a purchased one or more health quality credits into the account and updating the account to include health quality credit information about the purchased one or more health quality credits.

10. The method of claim 9, wherein health quality credit information comprises a credit identifier for each health quality credit in the account.

11. The method of claim 9, wherein a credit registration is associated with the health quality credits, and wherein the credit registration is updated to reflect ownership of the purchased one or more health quality credits by the health care provider.

12. The method of claim 11, wherein the credit registration is updated to reflect that the first credit is retired.

13. The method of claim 9, further comprising reporting transaction information associated with the purchased one or more health quality credits to a reporting system, wherein the transaction information comprises a volume and price of the purchased one or more health quality credits.

14. The method of claim 8, wherein the emission level is based on a number of potentially avoidable mortalities or a number of potentially avoidable complications.

15. The method of claim 8, wherein the health quality credit exchange is a voluntary exchange.

16. One or more non-transitory tangible computer storage media having computer-executable instructions embodied thereon that when executed provide a method using a health quality credit exchange system and an electronic health record (EHR) system for improving health care by a health care provider, the method comprising:
receiving an order to retire one or more health care quality credits, wherein the order is associated with a health care entity;
if there are a sufficient number of health quality offset credits in a health care quality credit account associated with the health care entity, apply a set of health quality offset credits to the order;
retire the set of health quality offset credits by annotating a unique credit identifier associated with each health quality offset credit of the set of health quality offset credits as retired; and
reduce a number of health quality offset credits in the health care quality credit account, wherein a retired health quality offset credit becomes no longer available for trading on a health quality exchange.

17. The one or more non-transitory tangible computer storage media of claim 16, wherein the number of the order to retire one or more health care quality credits is associated with a number of potentially avoidable patient outcomes.

18. The one or more non-transitory tangible computer storage media of claim 16, further comprising determining types of potentially avoidable patient outcomes in patient health care information, wherein an emission count is based on a type of the potentially avoidable patient outcomes.

19. The one or more non-transitory tangible computer storage media of claim 16, wherein each of the number of health quality offset credits comprises a unique identifier.

* * * * *